United States Patent
Yamauchi et al.

(10) Patent No.: US 9,592,307 B2
(45) Date of Patent: Mar. 14, 2017

(54) COMPOUND AND PHOTOACOUSTIC IMAGING CONTRAST MEDIUM CONTAINING THE COMPOUND

(71) Applicant: CANON KABUSHIKI KAISHA, Tokyo (JP)

(72) Inventors: Fumio Yamauchi, Kyoto (JP); Satoshi Ogawa, Kyoto (JP); Kengo Kanazaki, Kyoto (JP); Daisuke Sasaguri, Yokohama (JP); Atsushi Takahashi, Kyoto (JP); Masato Minami, Kawasaki (JP); Tatsuki Fukui, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 51 days.

(21) Appl. No.: 14/413,400

(22) PCT Filed: Jul. 17, 2013

(86) PCT No.: PCT/JP2013/004359
§ 371 (c)(1),
(2) Date: Jan. 7, 2015

(87) PCT Pub. No.: WO2014/013730
PCT Pub. Date: Jan. 23, 2014

(65) Prior Publication Data
US 2015/0157741 A1 Jun. 11, 2015

(30) Foreign Application Priority Data

Jul. 20, 2012 (JP) .................. 2012-161642

(51) Int. Cl.
| | | |
|---|---|---|
| A61K 49/00 | (2006.01) | |
| C07D 209/12 | (2006.01) | |
| A61K 49/22 | (2006.01) | |
| C07D 209/14 | (2006.01) | |
| C07D 209/60 | (2006.01) | |
| C07D 403/14 | (2006.01) | |
| C07K 7/06 | (2006.01) | |
| C07K 16/40 | (2006.01) | |

(52) U.S. Cl.
CPC .......... A61K 49/221 (2013.01); C07D 209/12 (2013.01); C07D 209/14 (2013.01); C07D 209/60 (2013.01); C07D 403/14 (2013.01); C07K 7/06 (2013.01); C07K 16/40 (2013.01); C07K 2317/622 (2013.01)

(58) Field of Classification Search
CPC .............................. A61K 49/00; A61K 49/221
See application file for complete search history.

(56) References Cited

U.S. PATENT DOCUMENTS

| 6,180,085 B1 | 1/2001 | Achilefu et al. |
|---|---|---|
| 6,350,431 B1 | 2/2002 | Snow et al. |
| 6,662,040 B1 | 12/2003 | Henrichs et al. |
| 7,025,949 B2 | 4/2006 | Licha et al. |
| 7,897,142 B2 | 3/2011 | Cuthbertson et al. |
| 8,227,610 B2 | 7/2012 | Janjic et al. |
| 8,273,325 B2 | 9/2012 | Tolleshaug et al. |
| 8,361,443 B2 | 1/2013 | Cuthbertson |
| 8,753,608 B2 | 6/2014 | Tabata et al. |
| 2001/0055567 A1 | 12/2001 | Licha et al. |
| 2009/0305410 A1 | 12/2009 | Mao et al. |
| 2012/0065384 A1 | 3/2012 | Nagano et al. |
| 2012/0114563 A1 | 5/2012 | Carter et al. |
| 2012/0244074 A1 | 9/2012 | Solbakken |
| 2013/0209367 A1 | 8/2013 | Ito et al. |
| 2013/0224121 A1 | 8/2013 | Fukui et al. |
| 2014/0227195 A1 | 8/2014 | Tabata et al. |
| 2015/0165071 A1 | 6/2015 | Takahashi et al. |
| 2015/0290345 A1 | 10/2015 | Takahashi et al. |

FOREIGN PATENT DOCUMENTS

| CA | 2211470 A1 | 8/1996 |
|---|---|---|
| CN | 101001870 A | 7/2007 |
| CN | 101641119 A | 2/2010 |
| CN | 101946171 A | 1/2011 |
| CN | 102438659 A | 5/2012 |
| WO | 98/02743 A1 | 1/1998 |
| WO | 98/48838 A1 | 11/1998 |
| WO | 2008/075968 A1 | 6/2008 |

(Continued)

OTHER PUBLICATIONS

Martin W. Brechbiel et al., Improved Specification Characteristics of PEGylated Indocyanine Green-Labeled Panitumumab: Revisiting the Solution and Spectroscopic Properties of a Near-Infrared Emitting anti-HER1 Antibody for Optical Imaging of Cancer, Bioconjugate Chem. 2010, 21, 2305-2312.*

Notification of the Second Office Action in Chinese Application No. 201380038553.X (dated Aug. 29, 2016).

Xueding Wang et al., "Noninvasive Photoacoustic Angiography of Animal Brains In Vivo with Near-Infrared Light and an Optical Contrast Agent," 29(7) Opt. Lett. 730-732 (Apr. 2004) (XP055079408).

Terukage Hirata et al., "Synthesis and Reactivities of 3-Indocyanine-green-acyl-1,3-thiazolidine-2-thione (ICG-ATT) as a New Near-Infrared Fluorescent-Labeling Reagent," 6(11) Bioorg. Med. Chem. 2179-2184 (Nov. 1998) (XP002922823).

Matthias A. Brun et al., "Semisynthesis of Fluorescent Metabolite Sensors on Cell Surfaces," 133(40) J. Am. Chem. Soc. 16235-16242 (Aug. 2011) (XP055079261).

(Continued)

*Primary Examiner* — Michael G Hartley
*Assistant Examiner* — Jagadishwar Samala
(74) *Attorney, Agent, or Firm* — Fitzpatrick, Cella, Harper & Scinto

(57) ABSTRACT

The present invention provides a compound which exhibits a high degree of accumulation into a tumor even when some extent of time has passed after performing administration and which facilitates an increase in the intensity of photoacoustic signal produced by the tumor.

A compound produced by bonding of a polyethylene glycol and a specific cyanine based compound.

14 Claims, 3 Drawing Sheets

(56) References Cited

FOREIGN PATENT DOCUMENTS

| WO | 2009/009105 A2 | 1/2009 |
|---|---|---|
| WO | 2009/078970 A1 | 6/2009 |
| WO | 2010/106169 A1 | 9/2010 |
| WO | 2011/073340 A1 | 6/2011 |
| WO | 2012/038489 A1 | 3/2012 |
| WO | 2014/013729 A1 | 1/2014 |
| WO | 2014/013732 A1 | 1/2014 |

OTHER PUBLICATIONS

Takahashi et al., U.S. Appl. No. 14/413,399, filed Jan. 7, 2015.
Takahashi et al., U.S. Appl. No. 14/413,402, filed Jan. 7, 2015.
First Office Action in Chinese Application No. 201380038553.X (dated Jan. 4, 2016).
Kohei Sano et al., "Short PEG-Linkers Improve the Performance of Targeted, Activatable Monoclonal Antibody-Indocyanine Green Optical Imaging Probes," 24(5) Bioconjugate Chem. 811-816 (Apr. 2013).

* cited by examiner

SEQUENCE LISTING

<160> NUMBER OF SEQ ID NOS: 3

<210> SEQ ID NO 1
<211> LENGTH: 739
<212> TYPE: DNA
<213> ORGANISM: Artificial Sequence
<220> FEATURE:
<223> OTHER INFORMATION: hu4D5-8scFv

<400> SEQUENCE: 1

| | | | | | |
|---|---|---|---|---|---|
| ccatggatat | ccagatgacc | cagtccccga | gctccctgtc | cgcctctgtg | ggcgataggg | 60 |
| tcaccatcac | ctgccgtgcc | agtcaggatg | tgaatactgc | tgtagcctgg | tatcaacaga | 120 |
| aaccaggaaa | agctccgaaa | ctactgattt | actcggcatc | cttcctctac | tctggagtcc | 180 |
| cttctcgctt | ctctggatcc | agatctggga | cggatttcac | tctgaccatc | agcagtctgc | 240 |
| agccggaaga | cttcgcaact | tattactgtc | agcaacatta | ctactcctcc | ccacgttcg | 300 |
| gacagggtac | caaggtggag | atcaaaggcg | gtggtggcag | cggtggcggt | ggcagcggcg | 360 |
| gtggcggtag | cgaggttcag | ctggtggagt | ctggcggtgg | cctggtgcag | ccagggggct | 420 |
| cactccgttt | gtcctgtgca | gcttctggct | tcaacattaa | agacacctat | atacactggg | 480 |
| tgcgtcaggc | cccgggtaag | ggcctggaat | gggttgcaag | gatttatcct | acgaatggtt | 540 |
| atactagata | tgccgatagc | gtcaagggcc | gtttcactat | aagcgcagac | acatccaaaa | 600 |
| acacagccta | cctgcagatg | aacagcctgc | gtgctgagga | cactgccgtc | tattattgtt | 660 |
| ctagatgggg | aggggacggc | ttctatgcta | tggactactg | gggtcaagga | accctggtca | 720 |
| ccgtctcctc | ggcggccgc | | | | | 739 |

<210> SEQ ID NO 2
<211> LENGTH: 256
<212> TYPE: PRT
<213> ORGANISM: Artificial Sequence
<220> FEATURE:
<223> OTHER INFORMATION: hu4D5-8scFv

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr

```
                    165                 170                 175
Asn Gly Tyr Thr Arg Tyr Ala Asp Ser Val Lys Gly Arg Phe Thr Ile
                180                 185                 190

Ser Ala Asp Thr Ser Lys Asn Thr Ala Tyr Leu Gln Met Asn Ser Leu
            195                 200                 205

Arg Ala Glu Asp Thr Ala Val Tyr Tyr Cys Ser Arg Trp Gly Gly Asp
        210                 215                 220

Gly Phe Tyr Ala Met Asp Tyr Trp Gly Gln Gly Thr Leu Val Thr Val
225                 230                 235                 240

Ser Ser Ala Ala Ala Leu Glu His His His His His His Gly Gly Cys
                245                 250                 255

<210> SEQ ID NO 3
<211> LENGTH: 12
<212> TYPE: PRT
<213> ORGANISM: Artificial Sequence
<220> FEATURE:
<223> OTHER INFORMATION: HER2 binding peptide

<400> SEQUENCE: 3

Met Ala Arg Ser Gly Leu Gly Gly Lys Gly Ser Cys
1               5                   10
```

COMPOUND AND PHOTOACOUSTIC IMAGING CONTRAST MEDIUM CONTAINING THE COMPOUND

TECHNICAL FIELD

The present invention relates to a compound and a photoacoustic imaging contrast medium containing the above-described compound.

BACKGROUND ART

A photoacoustic tomography (hereafter may be abbreviated to PAT) apparatus has been known as one of apparatuses to visualize the information of the inside of a living body. In a measurement by using the PAT apparatus, an arithmetic image of the matter distribution in the inside of a subject to be measured can be obtained by measuring the intensity and the production time of photoacoustic signals produced by a substance (light absorber), which has absorbed light, in the inside of the subject to be measured when the subject to be measured is irradiated with the light.

Here, any substance can be used as the light absorber insofar as the substance produces an acoustic wave because of absorption of the light in a living body. For example, it is possible that a blood vessel, a malignant tumor, or the like in a human body is employed as a light absorber. In addition, it is also possible that molecules of Indocyanine Green (hereafter may be abbreviated to ICG) and the like are administered to a body and are utilized as contrast media. ICG can be favorably used as a contrast medium in the PAT apparatus because of a small irradiation influence on a human body and high absorption of light, which is in the near-infrared wavelength region and which has a high permeability into a living body. Meanwhile, in the present specification, ICG refers to a compound represented by the following structure.

[Chem. 1]

(1)

In this regard, the counter ion is not necessarily $Na^+$, but any counter ion, e.g., $H^+$ or $K^+$, may be employed.

However, it has been known that the half-life of ICG in blood is about several minutes and, therefore, is very short.

NPL 1 reports an example in which photoacoustic imaging of cerebral blood vessel of a rat has been performed by using ICG alone. According to this report, the photoacoustic signal is reduced to the same level as that of the blood several tens of minutes after ICG have been administered to the blood alone and, therefore, it is indicated that the administered substance disappears from the blood promptly after administration.

As described above, ICG disappears from the blood several tens of minutes after being administered to the blood alone and it is considered that the degree of accumulation into a tumor is low when some time has passed after administration.

CITATION LIST

Non Patent Literature

NPL 1: Optics Letters, 29(7), 730 (2004)
NPL 2: Bioorganic & Medicinal Chemistry 6 (1998) 2179-2184

SUMMARY OF INVENTION

Accordingly, the present invention provides a compound which exhibits a high degree of accumulation into a tumor even when some time has passed after administration and which facilitates an increase in the intensity of photoacoustic signal produced by the tumor.

Solution to Problem

A compound according to an aspect of the present invention is represented by any one of the following formulae (I) to (IV).

[Chem.2]

$$A\text{-}L^1\text{-}(CH_2)_p\text{-}(OCH_2CH_2)_m\text{-}O\text{-}(CH_2)_q\text{-}L^2\text{-}A' \quad (I)$$

[Chem.3]

$$A\text{-}L^1\text{-}(CH_2)_p\text{-}(OCH_2CH_2)_m\text{-}O\text{-}(CH_2)_q L^2\text{-}M \quad (II)$$

[Chem.4]

$$N\text{-}L^1\text{-}(CH_2)_p\text{-}(OCH_2CH_2)_m\text{-}O\text{-}(CH_2)_q\text{-}L^2\text{-}A \quad (III)$$

[Chem.5]

$$A\text{-}L^1\text{-}(CH_2)_p\text{-}(OCH_2CH_2)_m\text{-}O\text{-}R \quad (IV)$$

In the formula (I), A and A' represent independently any one of the following formula (i) to formula (vi), and the symbol * in the following formulae (i) to (vi) is bonded to $L^1$ or $L^2$ in the formula (I).

In the formula (I), $L^1$ and $L^2$ represent independently a linker part which is any one of —NH—, —O—, —S—, and —CO— or which contains at least one of —NH—, —O—, —S—, and —CO—, p and q represent independently an integer of 1 to 5, and m represents an integer of 10 or more and 2,500 or less.

In the formula (II) and the formula (III), A represents any one of the following formulae (i) to (vi), and the symbol * in the following formulae (i) to (vi) is bonded to $L^1$ in the formula (II) or $L^2$ in the formula (III).

In the formula (II) and the formula (III), $L^1$ and $L^2$ represent independently a linker part which is any one of —NH—, —O—, —S—, and —CO— or which contains at least one of —NH—, —O—, —S—, and —CO—, p and q represent independently an integer of 1 to 5, and m represents an integer of 10 or more and 2,500 or less.

In the formula (II), in the case where L² is any one of —NH—, —O—, and —S—, M is a hydrogen atom, and in the case where L² is —CO—, M is a hydroxyl group.

In the formula (III), in the case where L¹ is any one of —NH—, —O—, and —S—, N is a hydrogen atom, and in the case where L¹ is —CO—, N is a hydroxyl group.

In the formula (IV), A represents any one of the following formula (i) to formula (vi), and the symbol * in the following formulae (i) to (vi) is bonded to L¹ in the formula (IV).

In the formula (IV), L¹ represents a linker part which is any one of —NH—, —O—, —S—, and —CO— or which contains at least one of —NH—, —O—, —S—, and —CO—, p represents an integer of 1 to 5, m represents an integer of 10 or more and 2,500 or less, and R represents any one of a hydrogen atom and a substituted or unsubstituted alkyl group having the carbon number of 1 to 5.

[Chem. 6]

(i)

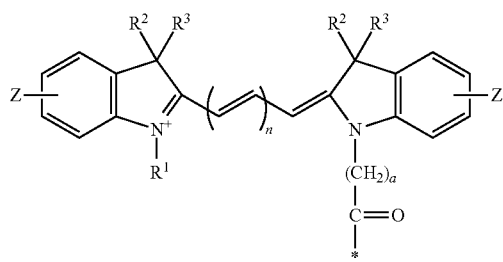

[Chem. 7]

(ii)

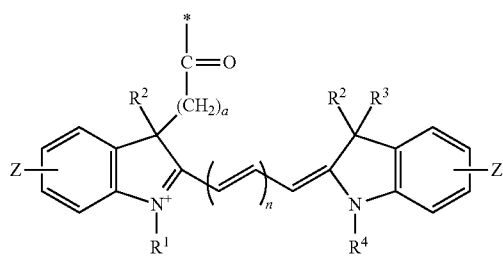

[Chem. 8]

(iii)

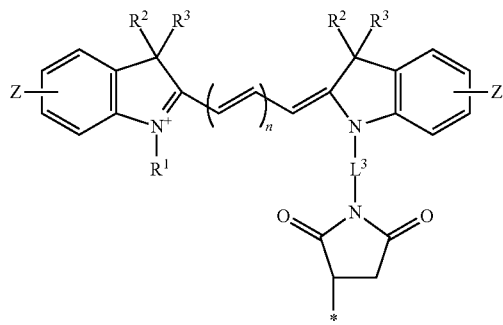

[Chem. 9]

(iv)

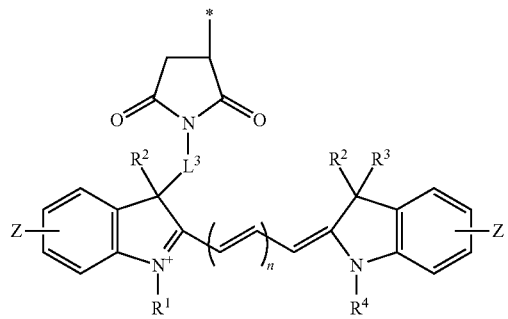

[Chem. 10]

(v)

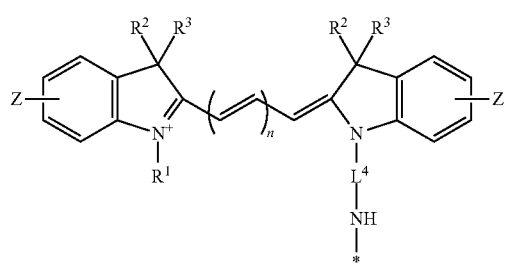

[Chem. 11]

(vi)

In the formula (i) to the formula (vi), Z forms a cyclic aromatic ring composed of a benz[e]indole ring, benz[f]indole ring, or benz[g]indole ring together with a hydrogen atom, a sulfonate group, or an indole ring bonded to Z, and furthermore, a hydrogen atom of the cyclic aromatic ring may be substituted with an alkyl group having the carbon number of 1 to 10, an alkoxy group having the carbon number of 1 to 10, or a sulfonate group.

In the formulae (i) to (vi), IV represents any one of an alkyl group having the carbon number of 1 to 10 and —(CH₂)$_b$—SO₃⁻ (b represents an integer of 1 to 10), in the case where R¹ is an alkyl group, a halogen ion or an organic acid ion may be contained as a counter ion, and R² and R³ represent independently any one of a hydrogen atom, an alkyl group having the carbon number of 1 to 10, an alkoxy group having the carbon number of 1 to 10, —(CH₂)$_b$—SO₃⁻ (b represents an integer of 1 to 10), and —(CH₂)$_b$—SO₃X (b represents an integer of 1 to 10 and X represents any one of sodium, potassium, ammonium, triethylammonium, lysine, and arginine).

In the formulae (i) and (ii), a represents an integer of 1 to 10.

In the formulae (i) to (vi), n represents 2 or 3.

In the formulae (ii), (iv), and (vi), R⁴ represents any one of an alkyl group having the carbon number of 1 to 10 and —(CH₂)$_b$—SO₃X (b represents an integer of 1 to 10 and X represents any one of sodium, potassium, ammonium, triethylammonium, lysine, and arginine).

In the formulae (iii) and (iv), $L^3$ represents a substituted or unsubstituted alkyl group having the carbon number of 1 to 10 and the chain of the alkyl group may include a carbonyl group, an amide group, an ester group, or a piperazyl group as a substituent.

In the formulae (v) and (vi), $L^4$ represents a substituted or unsubstituted alkyl group which has the carbon number of 1 to 10 and which may include a carbonyl group, an amide group, or an ester group as a substituent.

Advantageous Effects of Invention

According to aspects of the present invention, the compound has a structure in which a polyethylene glycol (hereafter may be abbreviated to PEG) and a cyanine based compound, e.g., ICG, are covalent-bonded. Consequently, the degree of accumulation into a tumor is high and the intensity of photoacoustic signals produced by the tumor is large as compared with those in the case where ICG is administered to a living body alone.

DESCRIPTION OF EMBODIMENTS

Figure 1:
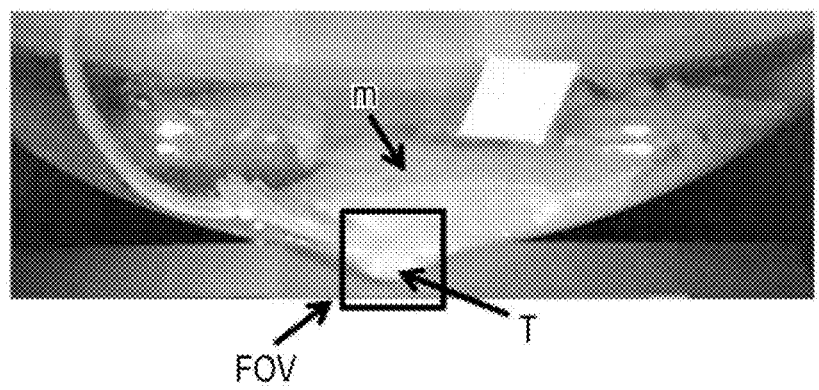
FIG. 1 is an optical photograph of a tumor-bearing mouse, where photoacoustic imaging was performed in an example according to an aspect of the present invention.

The embodiments according to aspects of the present invention will be described. A compound according to the present embodiment has a structure in which a specific cyanine based dye is bonded to a PEG, and the PEG is bonded through a substituent of a nitrogen atom present in an indole ring of the cyanine based dye. The compounds according to the present embodiment are specifically the compounds represented by the following formulae (I) to (IV).

[Chem.12]

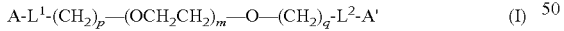

[Chem.13]

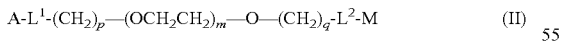

[Chem.14]

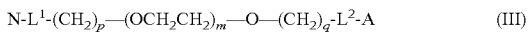

[Chem.15]

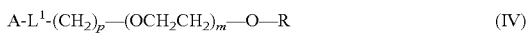

In the formula (I), A and A' represent independently any one of the following formula (i) to formula (vi), and the symbol * in the following formulae (i) to (vi) is bonded to $L^1$ or $L^2$ in the formula (I).

In the formula (I), $L^1$ and $L^2$ represent independently a linker part which is any one of —NH—, —O—, —S—, and —CO— or which contains at least one of —NH—, —O—, —S—, and —CO—, p and q represent independently an integer of 1 to 5, and m represents an integer of 10 or more and 2,500 or less.

In the formula (II) and the formula (III), A represents any one of the following formulae (i) to (vi), and the symbol * in the following formulae (i) to (vi) is bonded to $L^1$ in the formula (II) or $L^2$ in the formula (III).

In the formula (II) and the formula (III), $L^1$ and $L^2$ represent independently a linker part which is any one of —NH—, —O—, —S—, and —CO— or which contains at least one of —NH—, —O—, —S—, and —CO—, p and q represent independently an integer of 1 to 5, and m represents an integer of 10 or more and 2,500 or less.

In the formula (II), in the case where $L^2$ is any one of —NH—, —O—, and —S—, M is a hydrogen atom, and in the case where $L^2$ is —CO—, M is a hydroxyl group.

In the formula (III), in the case where $L^1$ is any one of —NH—, —O—, and —S—, N is a hydrogen atom, and in the case where $L^1$ is —CO—, N is a hydroxyl group.

In the formula (IV), A represents any one of the following formula (i) to formula (vi), and the symbol * in the following formulae (i) to (vi) is bonded to $L^1$ in the formula (IV).

In the formula (IV), $L^1$ represents a linker part which is any one of —NH—, —O—, —S—, and —CO— or which contains at least one of —NH—, —O—, —S—, and —CO—, p represents an integer of 1 to 5, m represents an integer of 10 or more and 2,500 or less, and R represents any one of a hydrogen atom and a substituted or unsubstituted alkyl group having the carbon number of 1 to 5.

In this regard, in the present specification, the symbol * represents the following mark in the structural formula.

[Chem. 16]

*

[Chem. 17]

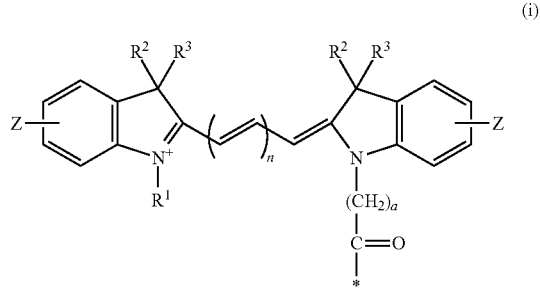

[Chem. 18]

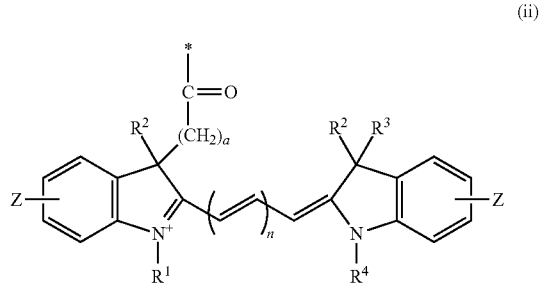

[Chem. 19]

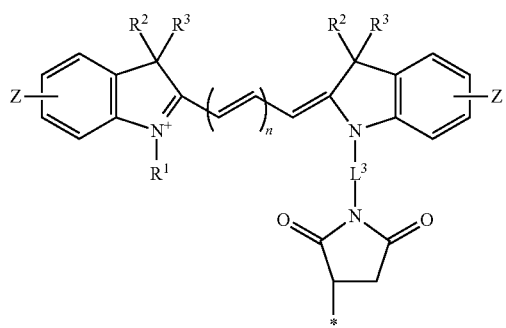

(iii)

[Chem. 20]

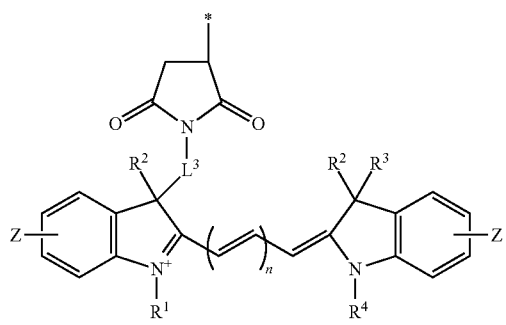

(iv)

[Chem. 21]

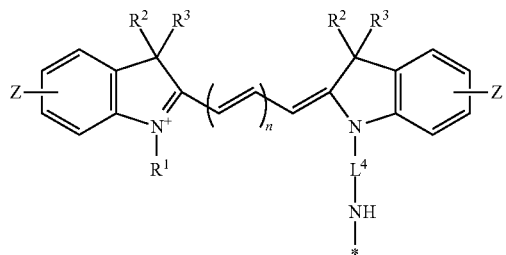

(v)

[Chem. 22]

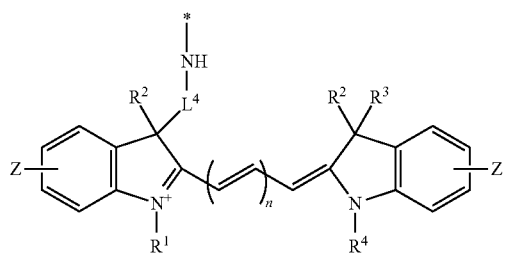

(vi)

In the formulae (i) to (vi), Z forms a cyclic aromatic ring composed of a benz[e]indole ring, benz[f]indole ring, or benz[g]indole ring together with a hydrogen atom, a sulfonate group, or an indole ring bonded to Z, and furthermore, a hydrogen atom of the cyclic aromatic ring may be substituted with an alkyl group having the carbon number of 1 to 10, an alkoxy group having the carbon number of 1 to 10, or a sulfonate group.

In the formulae (i) to (vi), $R^1$ represents any one of an alkyl group having the carbon number of 1 to 10 and —$(CH_2)_b$—$SO_3^-$ (b represents an integer of 1 to 10), in the case where $R^1$ is an alkyl group, a halogen ion, e.g., a chloride ion, a bromide ion, or an iodide ion, or an organic acid ion, e.g., an acetate ion, a tartrate ion, or a succinate ion, may be contained as a counter ion, and $R^2$ and $R^3$ represent independently any one of a hydrogen atom, an alkyl group having the carbon number of 1 to 10, an alkoxy group having the carbon number of 1 to 10, —$(CH_2)_b$—$SO_3$ (b represents an integer of 1 to 10), and —$(CH_2)_b$—$SO_3X$ (b represents an integer of 1 to 10 and X represents any one of sodium, potassium, ammonium, triethylammonium, lysine, and arginine).

In the formulae (i) and (ii), a represents an integer of 1 to 10.

In the formulae (i) to (vi), n represents 2 or 3.

In the formulae (ii), (iv), and (vi), $R^4$ represents any one of an alkyl group having the carbon number of 1 to 10 and —$(CH_2)_b$—$SO_3X$ (b represents an integer of 1 to 10 and X represents any one of sodium, potassium, ammonium, triethylammonium, lysine, and arginine).

In the formulae (iii) and (iv), $L^3$ represents any divalent group and is, for example, a substituted or unsubstituted alkyl group which has the carbon number of 1 to 10 and which may include a carbonyl group, an amide group, an ester group, a piperazyl group, or the like as a substituent.

In the formulae (v) and (vi), $L^4$ represents any divalent group and is, for example, a substituted or unsubstituted alkyl group which has the carbon number of 1 to 10 and which may include a carbonyl group, an amide group, an ester group, or the like as a substituent.

In the compound according to the present embodiment, m in the formulae (I) to (IV) is preferably an integer of 100 or more and 500 or less, and more preferably an integer of 200 or more and 400 or less.

In the formula (I), A and A' may be only one of the formulae (i) to (vi), or be a combination of the formulae (i) to (vi).

Both $L^1$ and $L^2$ in the formula (I) can be —NH— because bonding between A and $L^1$ and bonding between A' and $L^2$ are strong.

Both $L^1$ and $L^2$ can be —O— because it is considered that the dispersibility of the compound according to the present embodiment in an aqueous solution, e.g., a serum, increases.

Meanwhile, $L^1$ and $L^2$ may independently be a linker part containing at least one of —NH—, —O—, —S—, and —CO—. Here, the linker part refers to a part having a function to bond the ethylene glycol chain or the alkyl chain in the formula (I) to the formula (IV) to A or A'. Examples include bifunctional compounds, e.g., 1,6-bismaleimidohexane and succinimidyl trans-4-(N-maleimidylmethyl)-cyclohexane-1-carboxylate. Other examples may include alkyl groups having the carbon number of 1 to 10 and containing a carbonyl group, an amide group, an ester group, a piperazyl group, or the like. In other examples, polypeptides having any chain length may be used, and the polypeptides may be capture molecules described later. The polypeptide may form a covalent bond by using any one of a carbonyl group, an amino group, and a thiol group in the chain. For example, a N-PEG maleimide group and a thiol group may form a maleimide-thiol bond under a neutral condition at room temperature.

In the formula (i) and the formula (ii), a can be an integer of 2 to 6.

In the formula (i) to the formula (vi), b in $R^1$, $R^2$, and $R^3$ can be an integer of 2 to 6.

In the case where a in the formula (i) and the formula (ii) and b in the formula (i) to the formula (vi) are 6 or less, the hydrophobicity does not become high and, therefore, non-specific adsorption does not occur in a living body easily.

In the present embodiment, the above-described formula (i) can be represented by any one of the following formulae (i-1) to (i-6).

[Chem. 23]

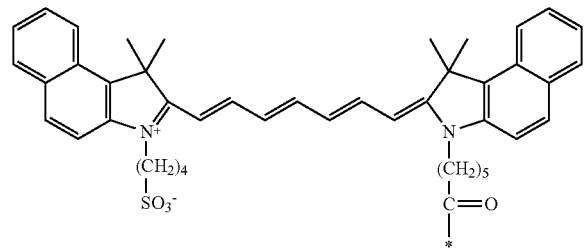

(i-1)

[Chem. 24]

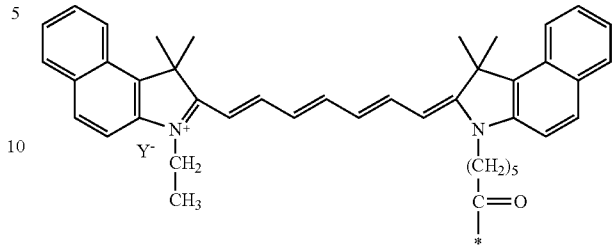

(i-2)

In the formula (i-2), $Y^-$ represents a halogen ion, e.g., a chloride ion, a bromide ion, or an iodide ion, or an organic acid ion, e.g., an acetate ion, a tartrate ion, or a succinate ion.

[Chem. 25]

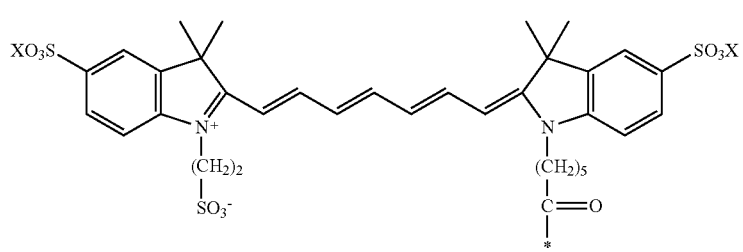

(i-3)

[Chem. 26]

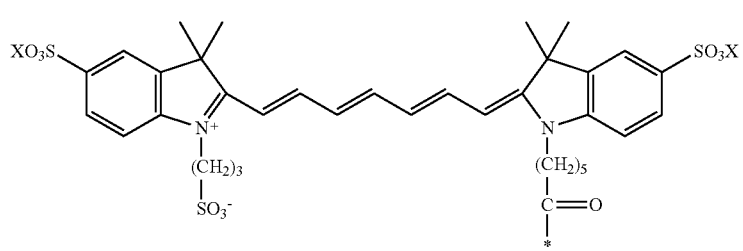

(i-4)

[Chem. 27]

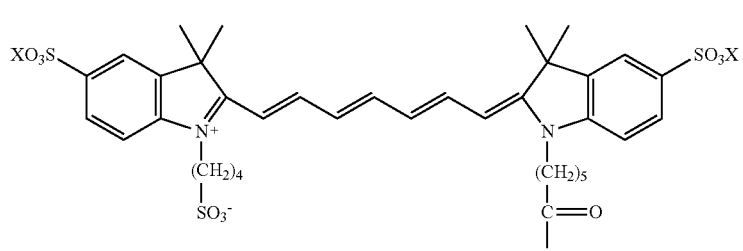

(i-5)

-continued
[Chem. 28]
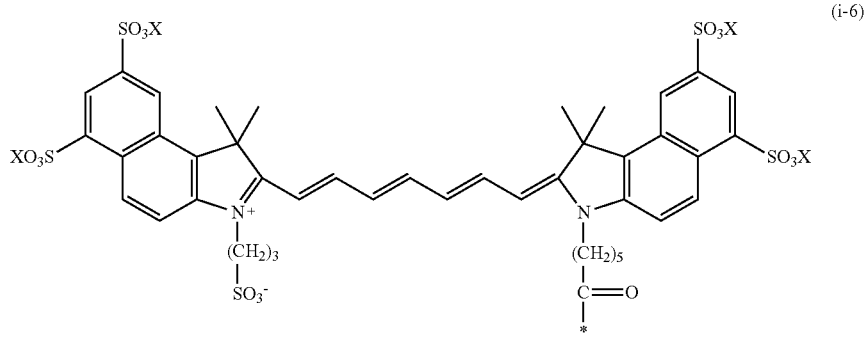
(i-6)
In the present embodiment, the above-described formula (ii) can be represented by any one of the following formulae (ii-1) and (ii-2).
[Chem. 29]
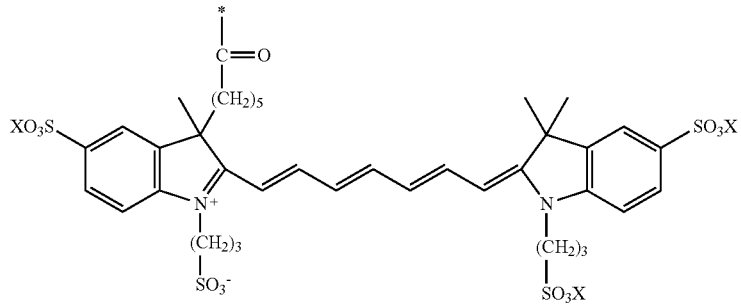
(ii-1)
[Chem. 30]
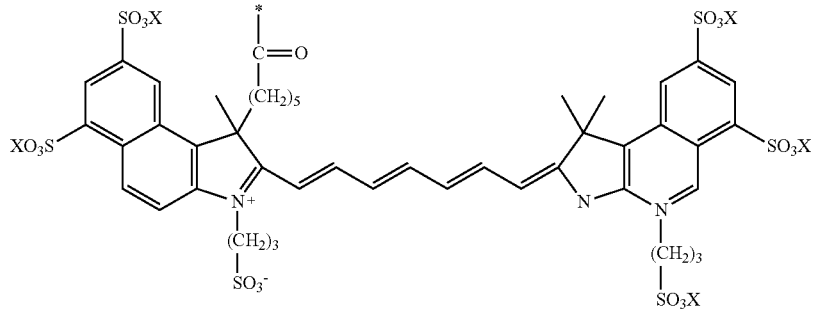
(ii-2)

In the present embodiment, the above-described formula (iii) can be represented by any one of the following formulae (iii-1) and (iii-2).

[Chem. 31]

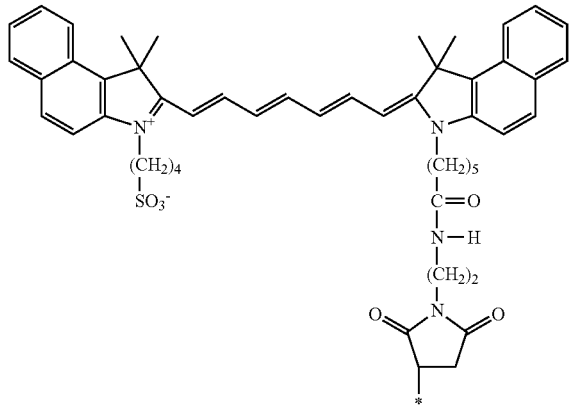

(iii-1)

[Chem. 32]

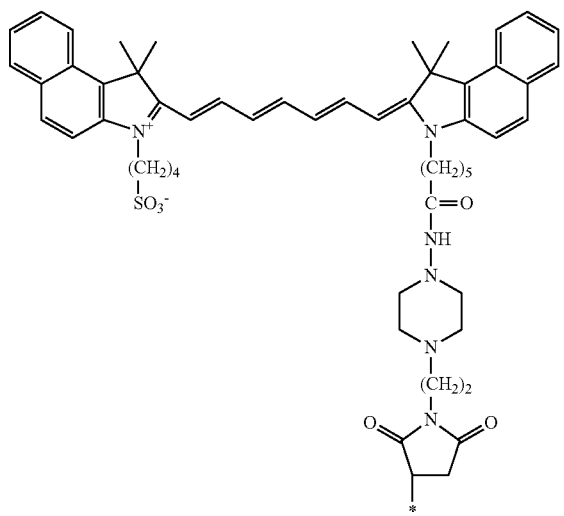

(iii-2)

In the present embodiment, the above-described formula (iv) can be represented by any one of the following formulae (iv-1) and (iv-2).

[Chem. 33]

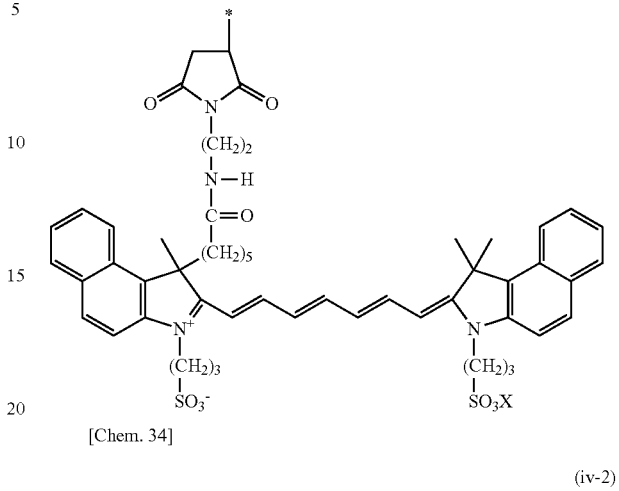

(iv-1)

[Chem. 34]

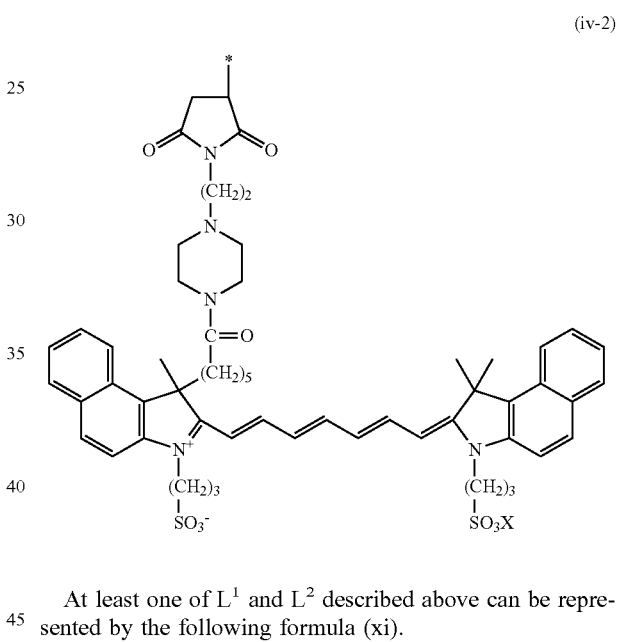

(iv-2)

At least one of $L^1$ and $L^2$ described above can be represented by the following formula (xi).

[Chem. 35]

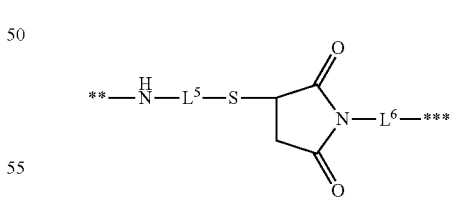

(xi)

In the formula (xi), $L^5$ represents a polypeptide or a single-chain antibody, —NH— represents a bond through an amino group of an amino acid in the polypeptide or the single-chain antibody, —S— represents a bond through a thiol group of an amino acid in the polypeptide or the single-chain antibody, $L^6$ represents an alkyl chain which has the carbon number of 1 to 10 and which includes a carbonyl group, an amide group, an ester group, a piperazyl group, or the like, the symbol ** is bonded to the above-described symbol *, and the symbol *** is bonded to the alkyl chain side or the ethylene glycol chain side of the formulae (I) to (IV).

In the formula (xi), $L^6$ can be represented by the following formula (xii),

—(CH$_2$)$_2$—C(=O)—NH— (xii)

In the formula (xii), carbon in the ethylene group is bonded to nitrogen in the maleimide group in the above-described formula (xi), and nitrogen in —NH— is bonded to the symbol * in the above-described formula (xi). That is, the ethylene group side is bonded to the nitrogen atom of the maleimide group and the amide side is bonded to the symbol *.

In addition, the compound according to the present embodiment may be bonded to another dye.

The compound according to the present embodiment may include a capture molecule which is specifically bonded to a target part.

Method for Preparing Compound

The compound according to the present embodiment is prepared by bonding the PEG to the specific cyanine based compound through their respective functional groups by a known coupling reaction. For example, bonding to the PEG is performed through a substituent of the nitrogen atom present in the nitrogen-containing heterocyclic ring of the specific cyanine based compound. Bonding can be performed through the amino group of the PEG having an amino group and the sulfosuccinimide ester (may be abbreviated to Sulfo-OSu) included in the specific cyanine based compound. The specific cyanine based dye bonded to the PEG may be washed and refined by a known refining method, e.g., an ultrafiltration method or size exclusion column chromatography. As for the bonding between the PEG and the specific cyanine based compound, the above-described functional group, e.g., an amino group, included in the PEG may be bonded directly to the specific cyanine based compound, or the PEG may be bonded to the specific cyanine based compound through various cross-linking agents (cross-linkers).

The compound according to the present embodiment can be prepared by covalent-bonding the PEG having a molecular weight of 1,000 or more and including at least one amino group to Indocyanine Green-N-butanoic acid sulfosuccinimide ester (ICG-Sulfo-OSu (registered trademark) (produced by DOJIJDO LABORATORIES).

PEG

The PEG used for preparing the compound according to the present embodiment is a water-soluble polymer and exerts effects of increasing a serum half-life of protein, reducing the immunogenicity, and the like. The molecular weight of the PEG is preferably within the range of 400 or more and 100,000 or less, and further preferably 20,000 or more. It is believed that if the molecular weight is 20,000 or more, a larger amount of PEG can be accumulated in a tumor part as compared with a normal part in a living body on the basis of an enhanced permeability and retention (EPR) effect. If the molecular weight is 20,000 or more, excretion from a kidney is suppressed and, therefore, it is expected that the retentivity in blood increases as compared with a PEG having a molecular weight of less than 20,000. As the molecular weight of PEG increases, the viscosity of the solution increases, so that the molecular weight of PEG is preferably 100,000 or less.

The PEG according to the present embodiment has at least one reactive functional group, which is able to be covalent-bonded to the specific cyanine based compound, per PEG molecule. The reactive functional group may be selected appropriately in accordance with the functional group included in the dye to be bonded. Examples of reactive functional groups can include an amino group, a hydroxyl group, a thiol group, a carbonyl group, a sulfhydryl group, an epoxy group, a glycidyl group, a N-succinimidyloxy group, a N-sulfosuccinimidyloxy group, and a N-maleimidoalkyl group.

Specific Cyanine Based Compound

In the present embodiment, the structure of the specific cyanine based compound is represented by, for example, the following formula (V).

B—B' (V)

In the formula (V), B represents the above-described formula (i) or the above-described formula (ii).

In the formula (V), B' represents any one of the following formulae (vii) to (x).

[Chem. 36]

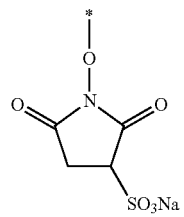
(vii)

[Chem. 37]

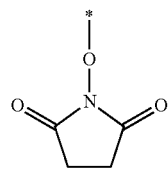
(viii)

[Chem. 38]

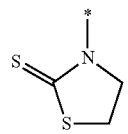
(ix)

[Chem. 39]

*—OH (x)

An example of the above-described formula (V) can be any one of the compound represented by the following formula (2) (ICG-Sulfo-OSu (produced by Dojindo Laboratories, registered trademark)), the compound represented by the following formula (3), the compound represented by the following formula (4), the compound represented by the following formula (5), the compound represented by the following formula (6), the compound represented by the following formula (7), and the compound represented by the following formula (8).

[Chem. 40]
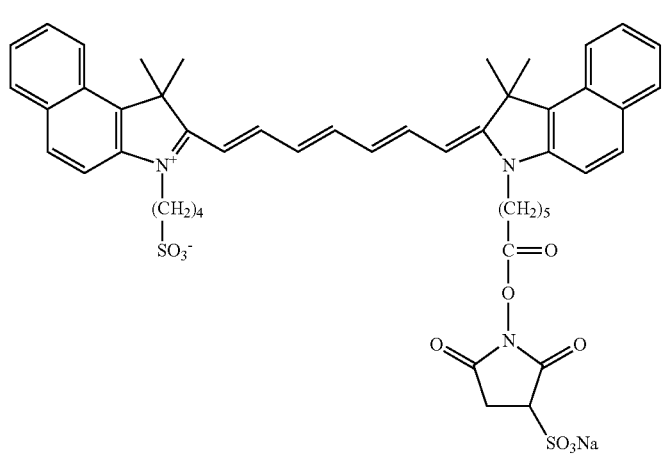
(2)
[Chem. 41]
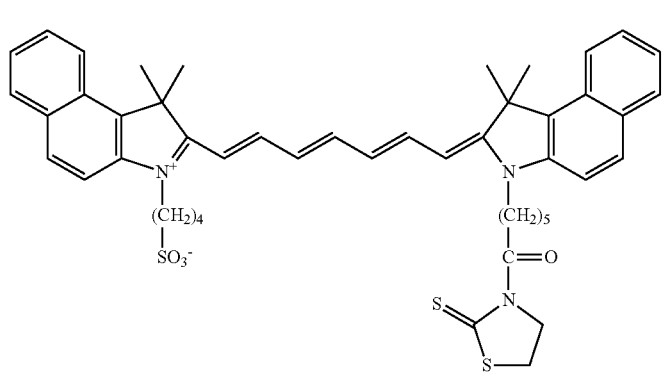
(3)
[Chem. 42]
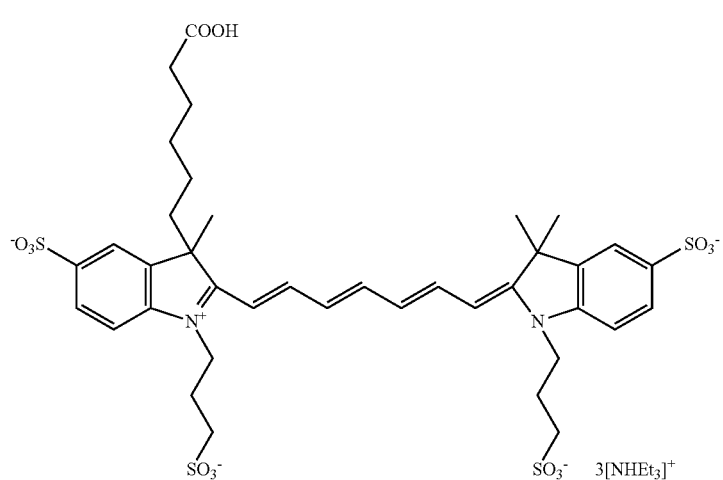
(4)

[Chem. 43]
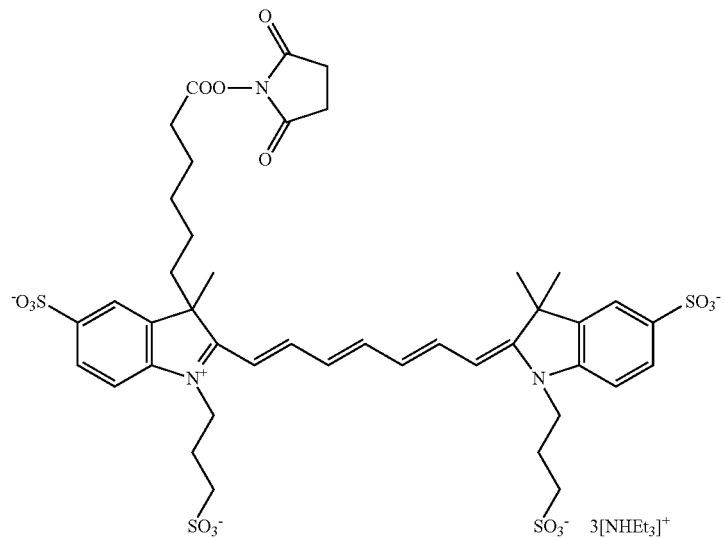
(5)
[Chem. 44]
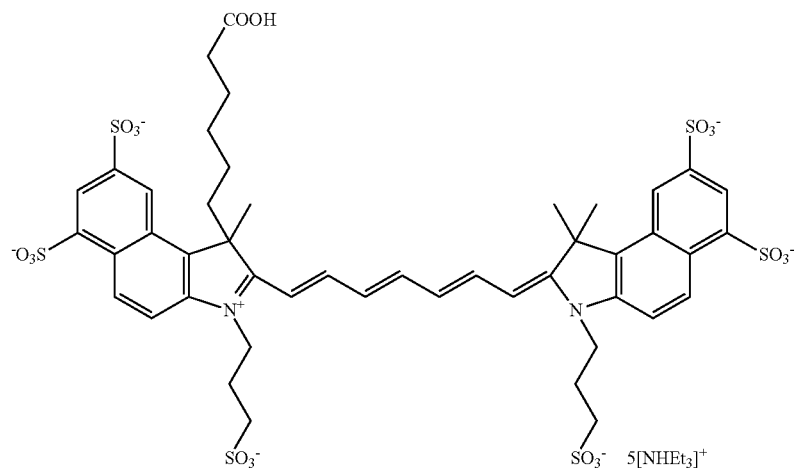
(6)
[Chem. 45]
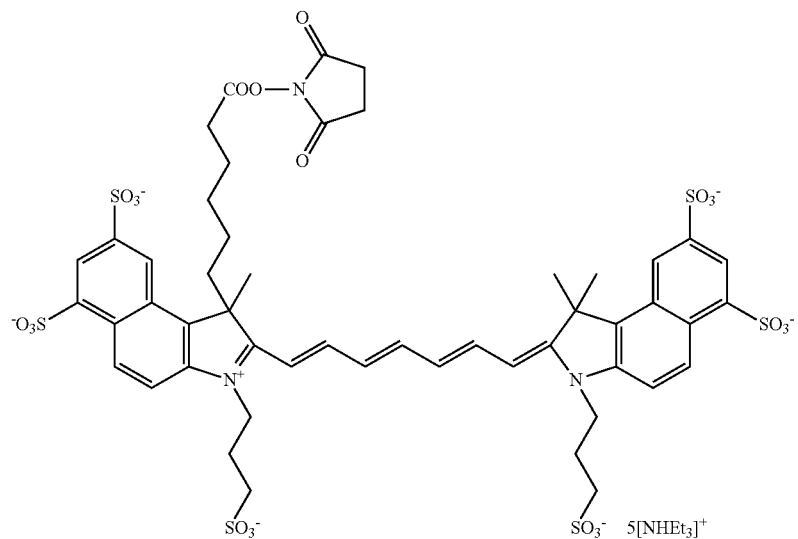
(7)

[Chem. 46]

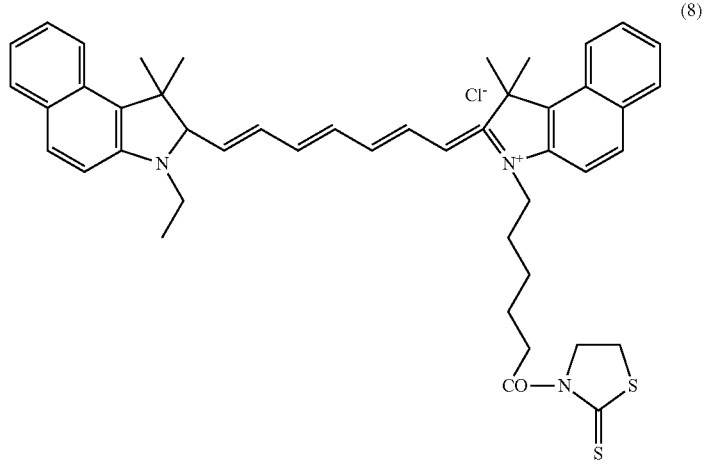

(8)

Photoimaging Contrast Medium

The photoimaging contrast medium according to the present embodiment includes the compound according to the present embodiment and a dispersion medium. In this regard, the photoimaging contrast medium according to the present embodiment may contain pharmacologically allowable additives, for example, a vasodilator, as necessary, in addition to the compound according to the present embodiment.

The dispersion medium is a liquid substance to disperse the compound according to the present embodiment, and examples include physiological saline, distilled water for injection, phosphate buffered saline, and glucose aqueous solution. As for the photoimaging contrast medium according to the present embodiment, the compound according to the above-described present embodiment may be dispersed in this dispersion medium in advance or the particles according to the present embodiment and the dispersion medium may be made into a kit so as to be used for administration to a living body after the particles are dispersed into the dispersion medium.

The photoimaging in the present embodiment refers to imaging by application of light. That is, acoustic waves, fluorescence, and the like are emitted by application of light to parts other than the PEG in the photoimaging contrast medium according to the present embodiment. Photoacoustic imaging is performed by detecting the emitted acoustic waves and fluorescent imaging is performed by detecting the emitted fluorescence. In this regard, the photoacoustic imaging is a concept containing photoacoustic tomography.

The photoimaging contrast medium according to the present embodiment may be called a fluorescent imaging contrast medium in the case of use for the fluorescent imaging, and may be called a photoacoustic imaging contrast medium in the case of use for the photoacoustic imaging.

A larger amount of photimaging contrast medium according to the present embodiment may be accumulated into a tumor part as compared with a normal part in a living body taking advantage of the EPR effect, when being administered to the living body. As a result, when the photoimaging contrast medium according to the present embodiment is administered to the living body and, thereafter, light is applied to the living body to detect an acoustic wave from the living body, an acoustic wave produced by a tumor part is allowed to become larger than an acoustic wave produced by a normal part.

The photoimaging contrast medium according to the present embodiment may also be used for imaging of a lymph node and, in particular, can be used as a contrast medium of a sentinel lymph node. This is because the size is large as compared with a single dye and, thereby, retention in the sentinel lymph node occurs easily, so that an improvement in accumulation is expected.

Capture Molecule

The capture molecule in the present embodiment refers to, for example, a substance specifically bonded to a target part, e.g., a tumor, or a substance specifically bonded to a substance present around a target part, and may be selected optionally from, for example, living body molecules and chemical substances, e.g., drugs. Specific examples include antibodies, antibody fragments, artificial antibodies, e.g., single-chain antibodies, enzymes, biologically active peptides, glycopeptides, saccharides, lipids, and molecular recognition compounds. These substances may be used alone or a plurality of them may be used in combination. In the case where a compound, according to the present embodiment, chemically bonded to the capture molecule is used, specific detection of a target part and tracing of dynamic behavior, localization, drug efficacy, metabolism, and the like of the target substance may be performed.

Addition Agent

The photoimaging contrast medium according to the present embodiment may contain an addition agent used in freeze-drying. Examples of addition agents include glucose, lactose, mannitol, polyethylene glycol, glycine, sodium chloride, and sodium hydrogen phosphate. One type of addition agent may be used alone or some types may be used in combination.

Photoacoustic Imaging Method

A method for detecting the compound, according to the present embodiment, administered to a living body by using a photoacoustic imaging apparatus will be described. The method for detecting the compound according to the present embodiment includes the following steps (a) and (b). However, the photoacoustic imaging method according to the present embodiment may include steps other than the steps described below.

(a) A step to apply light in a wavelength region of 600 nm to 1,300 nm to a specimen which has been administered the compound according to the present embodiment (b) A step to detect an acoustic wave produced by the above-described compound present in the inside of the above-described specimen In addition, the compound according to the present embodiment may include a step to reconfigure the spatial photoacoustic signal intensity distribution on the basis of the wavelength, phase, time information, and the like of the acoustic wave obtained in the above-described step (b). In this regard, a three-dimensional image reconfiguration may be performed on the basis of the wavelength, phase, and time information of the photoacoustic signal obtained in the above-described step (b). The data obtained by the image reconfiguration may take on any form insofar as the positional information of the intensity distribution of the photoacoustic signal is grasped. For example, the photoacoustic signal intensity may be expressed in a three-dimensional space or the photoacoustic signal intensity may be expressed on a two-dimensional plane. It is also possible that pieces of information is acquired from the same observation subject by different imaging methods and the relationship in positional correspondence between those pieces of information and the photoacoustic intensity distribution is acquired.

In the above-described step (a), a specimen which has been administered the compound according to the present embodiment by a method of oral administration, injection, or the like may be used.

In the above-described step (b), the apparatus to emit light to be applied to the specimen and the apparatus to detect the photoacoustic signal produced by the compound according to the present embodiment are not specifically limited.

The light source to apply the light to the specimen in the above-described step (b) is not specifically limited insofar as laser pulse light with at least one wavelength selected from the range of 600 nm to 1,300 nm is applied to the above-described specimen. Examples of apparatuses to apply the laser pulse light include a titanium sapphire laser (LT-2211-PC, produced by Lotis), OPO laser (LT-2214 OPO, produced by Lotis), and an alexandrite laser.

The apparatus to detect an acoustic wave is not specifically limited and various apparatuses may be used. For example, a commercially available photoacoustic imaging apparatus (Nexus128, produced by Endra Inc.) may be employed.

The imaging method by using the compound according to the present embodiment may perform imaging of a predetermined part, e.g., a tumor, a lymph node, or a blood vessel, through the above-described steps (a) and (b).

EXAMPLES

The present invention will be described below in further detail with reference to examples, although the present invention is not limited to these examples. In this regard, hereafter Mw represents a molecular weight. The typical structure of each of the samples, M5k-ICG, M10k-ICG, M20k-ICG, M30k-ICG, and M40k-ICG, which are prepared in the present example, is represented by the formula (P1) or the formula (I-1), and the molecular weights of polyethylene glycols are 5 k, 10 k, 20 k, 30 k, and 40 k, respectively. The structure of DE-200PA is represented by the formula (II) and the molecular weight of polyethylene glycol is 20 k.

[Chem. 47]

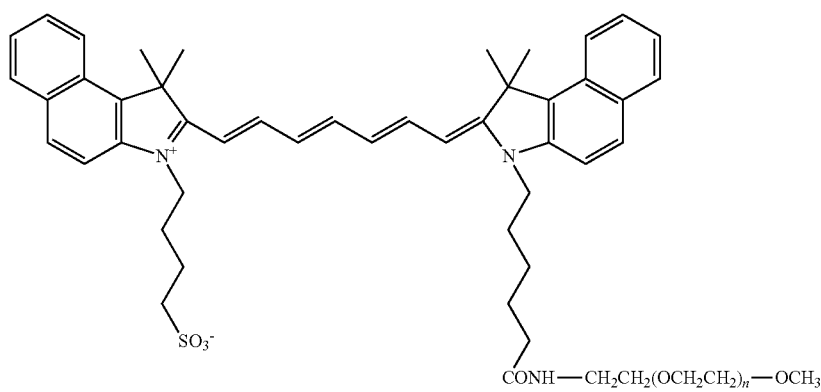

(I-1)

-continued

[Chem. 48]

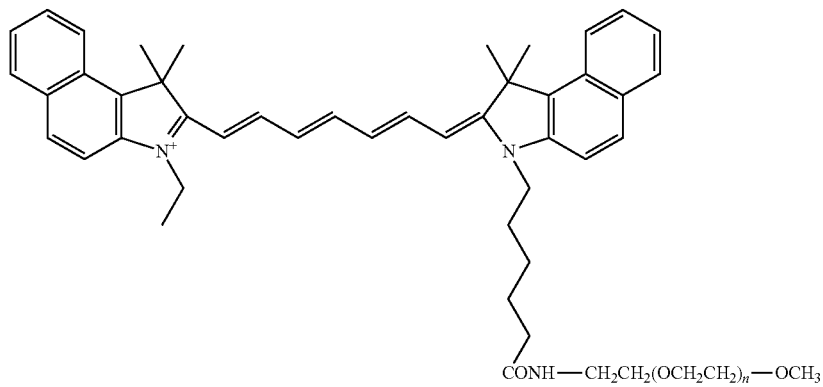

(I-2)

[Chem. 49]

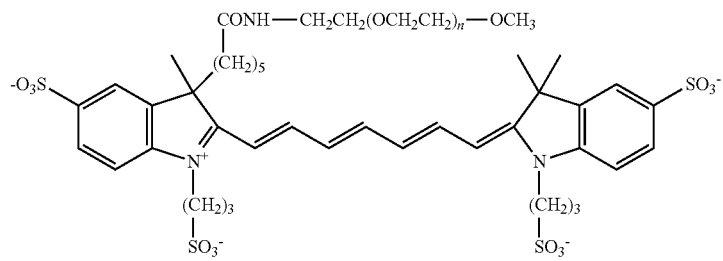

(I-3)

[Chem. 50]

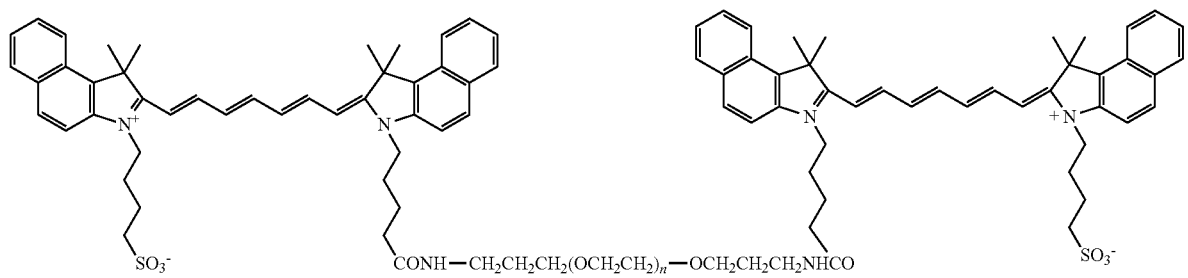

(II)

Example 1 to Example 4

Covalent Bond of Specific Cyanine Based Compound and PEG 1

As for the specific cyanine based compound according to the present embodiment, ICG-Sulfo-OSu (produced by Dojindo Laboratories) was used, and 1 mg (1.25 micromoles) of ICG-Sulfo-OSu was dissolved into 100 microliters of DMSO. Meanwhile, various PEGs were weighed into 1.5-mL plastic tubes. PEG was dissolved by 50 mM carbonate buffer (pH 9.0), so that the $NH_2$ concentration was specified to be 0.625 mM. Various PEGs employed here were monoamine straight chain ME-050EA (produced by NOF CORPORATION, Mw 5,000), monoamine straight chain ME100EA (produced by NOF CORPORATION, Mw 10,000), monoamine straight chain ME-200EA (produced by NOF CORPORATION, Mw 20,000), and diamine straight chain DE-200PA (produced by NOF CORPORATION, Mw 20,000). Those are summarized in Table 1.

TABLE 1

| | Product name of PEG employed | Molecular weight | The number of $NH_2$ per PEG | PEG weight (mg) | Amount of $NH_2$ (micromoles) | Carbonate buffer (microliters) | $NH_2$ concentration (mM) |
|---|---|---|---|---|---|---|---|
| Example 1 | DE-200PA | 20000 | 2 | 2.5 | 0.25 | 400 | 0.625 |
| Example 2 | ME-050EA | 5000 | 1 | 1.25 | 0.25 | 400 | 0.625 |
| Example 3 | ME-100EA | 10000 | 1 | 2.5 | 0.25 | 400 | 0.625 |
| Example 4 | ME-200EA | 20000 | 1 | 5 | 0.25 | 400 | 0.625 |

The structures of ME-050EA, ME-100EA, and ME-200EA employed as described above are represented by the following formula (p1), and the molecular weights are 5 k, 10 k, and 20 k, respectively.

$$CH_3O-(CH_2CH_2O)_m-CH_2CH_2NH_2 \quad (p1)$$

In the present specification, k represents 1,000, and for example, 5 k represents 5,000.

The structure of DE-200PA employed as described above is represented by the following formula (p2), and the molecular weight is 20 k.

$$X-(CH_2CH_2O)_m-X \quad (p2)$$

In the above-described formula (p2), X is represented by the following formula.

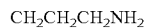
$$CH_2CH_2CH_2NH_2$$

Addition of 20 microliters ([ICG-Sulfo-OSu]=0.25 micromoles) of solution, ICG-Sulfo-OSu in DMSO, to a solution (400 microliters), PEG in carbonate buffer, was performed. ICG-Sulfo-OSu was allowed to react with a PEG at a molar ratio of 1. The concentration of ICG-Sulfo-OSu at the time of reaction was specified to be 0.6 mM. After rotational agitation was performed at room temperature for 24 hours under light shielding condition, the reaction solution was filtrated with a 0.22-micrometer syringe filter, so as to obtain a compound in which the specific cyanine based compound and the PEG were covalent-boned. The resulting compounds were stored at 4 degrees Celsius under light shielding condition.

Hereafter, the compounds produced by covalent bonding of monoamine straight chain ME-050EA, monoamine straight chain ME-100EA, monoamine straight chain ME-200EA, and diamine straight chain DE-200PA with ICG-Sulfo-OSu are abbreviated to M5k-ICG, M10k-ICG, M20k-ICG, and D20k-ICG2, respectively, as shown in Table 2. Likewise, a compound (hereafter abbreviated to ICG-Gly) was synthesized by reacting ICG-Sulfo-OSu with glycine at a molar ratio of 1:1, so as to serve as a reference sample (Table 2).

In this regard, the term "monoamine straight chain" refers to that one amino group per molecule of straight chain PEG is included, and the term "diamine straight chain" refers to that two amino groups per molecule of straight chain PEG are included. The number of amino groups is the same as the number of bonds possible for ICG-Sulfo-OSu to make.

TABLE 2

| | Product name of PEG employed | Sample name | Molecular weight | Form |
|---|---|---|---|---|
| Example 1 | DE-200PA | D20k-ICG2 | 20000 | diamine straight chain |
| Example 2 | ME-050EA | M5k-ICG | 5000 | monoamine straight chain |
| Example 3 | ME-100EA | M10k-ICG | 10000 | monoamine straight chain |
| Example 4 | ME-200EA | M20k-ICG | 20000 | monoamine straight chain |
| Reference example | ICG-Sulfo-OSu | ICG-Gly | 800 (molecular weight of glycine) | |

Measurement of Absorbance

Absorbances of solutions of M5k-ICG, M10k-ICG, M20k-ICG, D20k-ICG2, and ICG-Gly were measured. Dilution was performed with 50 mM of 4-(2-hydroxyethyl)-1-piperazineethanesulfonic acid (HEPES) solution, and absorbances at 700 nm and 785 nm were measured. The absorption at 700 nm is absorption by a dye in an association state. Meanwhile, absorption at 785 nm is absorption by a dye present as a monomer. Therefore, the ratio of absorption at 700 nm to absorption at 785 nm (abbreviated to 700/785) serves as an indicator of the association state of the dye. It is considered that as this value becomes large, the proportion of dyes associated with each other becomes large. The absorbance at 785 nm of the reaction solution was calculated by multiplying the above-described absorbance at 785 nm by the dilution ratio. The dye concentration of the reaction solution was calculated by dividing the resulting absorbance at 785 nm of the reaction solution by the molar absorption coefficient of $1.2 \times 10^5$ ($M^{-1} \times cm^{-1}$) of the dye. Table 3 shows the measurement results of absorbances.

As for ICG-Gly, green precipitates were observed during the reaction. Meanwhile, as for four types of M5k-ICG, M10k-ICG, M20k-ICG, and D20k-ICG2, no precipitates were observed during the reaction, and it was made clear that good dispersibility in water was exhibited. Although the dye was unstable in the water by itself, it was indicated that the stability of the dye was improved by covalent-bonding with the PEG.

TABLE 3

| | Sample name | Dilution ratio (HEPES) | Absorbance at 700 nm | Absorbance at 785 nm | Absorbance at 700 nm/absorbance at 785 nm | Absorbance of reaction solution at 785 nm | Dye concentration of reaction solution (mM) |
|---|---|---|---|---|---|---|---|
| Example 1 | D20k-ICG2 | 100 | 0.26 | 0.41 | 0.63 | 41 | 0.34 |
| Example 2 | M5k-ICG | 100 | 0.14 | 0.52 | 0.27 | 52 | 0.43 |
| Example 3 | M10k-ICG | 100 | 0.22 | 0.49 | 0.45 | 49 | 0.41 |
| Example 4 | M20k-ICG | 100 | 0.27 | 0.58 | 0.47 | 58 | 0.48 |
| Reference example | ICG-Gly | 100 | 0.23 | 0.33 | 0.7 | 33 | 0.28 |

Evaluation of Tumor Accumulation

In order to evaluate the tumor accumulation of the compound prepared as described above, M5k-ICG, M10k-ICG, M20k-ICG, D20k-ICG2, and ICG-Gly were administered to tail veins of tumor-bearing mice which had been transplanted an N87 cell line. The amount of administration was 13 nmol in terms of the amount of dye. The mouse was euthanized with a carbon dioxide gas 24 hours after the administration. Thereafter, an N87 tumor tissue was enucleated. The tumor tissue was transferred to a plastic tube, 1% Triton-X100 aqueous solution 1.25 times the tumor tissue in weight was added, and a homogenate was produced using a plastic pestle. Subsequently, dimethyl sulfoxide (DMSO) 20.25 times the tumor tissue in weight was added. The amount of dye in the tumor tissue was quantified by using IVIS (registered trademark) Imaging System 200 Series (produced by XENOGEN) and measuring the fluorescent intensity of the homogenate solution in the state of the plastic tube. The proportion of the amount of migration of the dye to the tumor tissue relative to the amount (dye 13 nmol) of administration (% injected dose: abbreviated to % ID) per unit weight of the tumor tissue is shown in Table 4 as the amount of tumor accumulation of the compound (% ID/g).

As a result, the tumor accumulation of ICG-Gly serving as a reference was 0.6% ID/g, whereas M5k-ICG, M10k-ICG, M20k-ICG, and D20k-ICG2 exhibited 1.1, 1.4, 5.2, and 7.0% ID/g, respectively, so that the tumor accumulation increased along with an increase in the molecular weight. This is believed to be the result of an increase in the molecular size along with the increase in the molecular weight and restriction of excretion thereof from a kidney. Furthermore, when M20k-ICG and D20k-ICG2, which have a molecular weight of 20,000, are compared, the tumor accumulation of the diamine straight chain (compound in which dyes are bonded to both terminals of PEG) was higher than that of the monoamine straight chain. It is considered that the tumor accumulation increased because the diamine straight chain PEG had the larger number of dyes per PEG molecule and, as a result, the stability of the dye was improved on the basis of hydrophobic association in the PEG molecular chain or between molecular chains through the dye, the apparent molecular size was changed, or the like. As with the results described above (measurement of absorbance), it was indicated that the tumor accumulation was enhanced by covalent bonding with the PEG as compared with a single dye, and it was indicated that the PEG molecular weight and the PEG form were important parameters with respect to the tumor accumulation.

TABLE 4

| Sample name | Tumor accumulation (% ID/g) |
|---|---|---|
| Example 1 | D20k-ICG2 | 7 |
| Example 2 | M5k-ICG | 1.1 |
| Example 3 | M10K-ICG | 1.4 |
| Example 4 | M20k-ICG | 5.2 |
| Reference example | ICG-Gly | 0.6 |

Photoacoustic Imaging of Tumor Part

Figure 2:
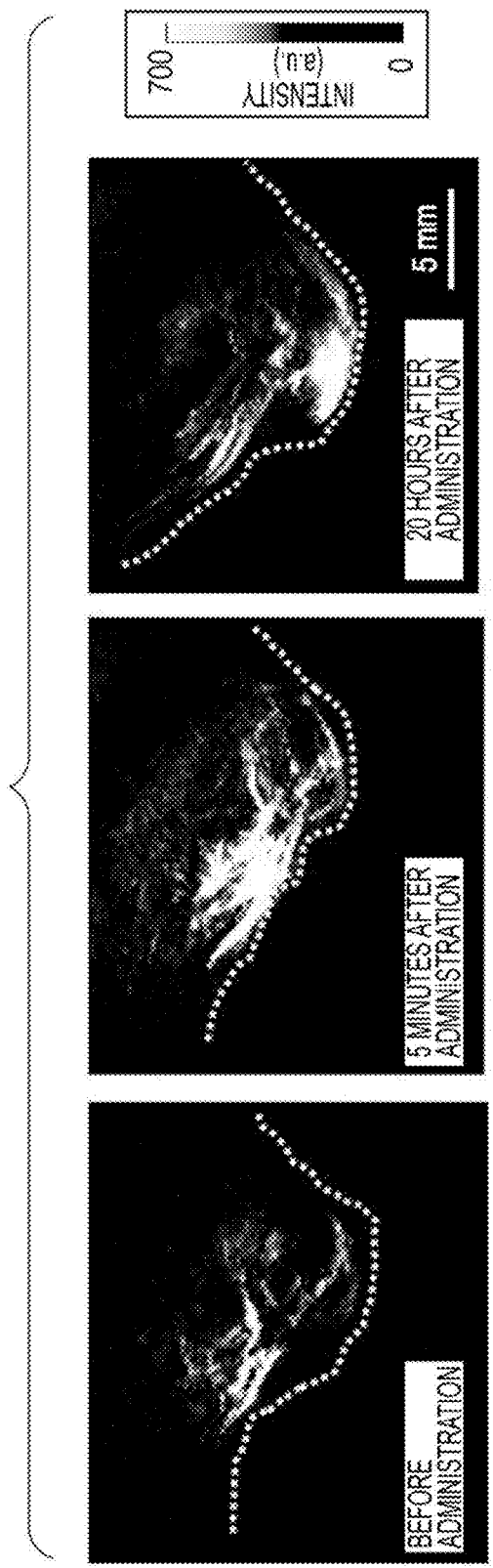
FIG. 2 shows images obtained by photoacoustic imaging performed in an example according to an aspect of the present invention.

In order to examine the performance of imaging of a tumor, in the same manner as employed in [Evaluation of Tumor Accumulation], M20k-ICG was administered to a tail vein of a tumor-bearing mouse which had been transplanted an N87 cell line. The amount of administration was 65 nmol in terms of the amount of dye. Photoacoustic imaging (irradiation laser wavelength 785 nm) was performed 5 minutes after administration and 20 hours after administration. FIG. 1 is an optical photograph of a mouse in photoacoustic imaging and shows a mouse (m in the drawing) placed under anesthesia. In the drawing, FOV is a tumor portion (T in the drawing) of a mouse subjected to subcutaneous transplantation and is an observation region (2 cm×2 cm×2 cm) of the photoacoustic imaging. FIG. 2 shows the results of the photoacoustic imaging of the tumor portion and Table 5 shows the photoacoustic intensity ratio of the tumor portion, where the photoacoustic intensity before administration was specified to be 1. In the drawing, white dotted lines indicate the outlines of the mouse. As is clear from FIG. 2 and Table 5, the photoacoustic signal intensity of the tumor portion increased just after the administration (5 minutes after) significantly, the photoacoustic signal was maintained even 20 hours after the administration, and the photoacoustic signal 2.6 times the signal before the administration was observed. Consequently, it was ascertained that an image on the basis of the photoacoustic imaging of a tumor part was able to be obtained by using the compound according to the example of an aspect of the present invention.

TABLE 5

| | Photoacoustic intensity ratio in tumor part |
|---|---|
| Before administration | 1 |
| 5 minutes after administration | 3.5 |
| 20 hours after administration | 2.6 |

Preparation of Marker

A solution, ICG-Sulfo-OSu in DMSO, was added to a solution (pH 7.1), the PEG in HEPES. ICG-Sulfo-OSu and the PEG were reacted at a reaction molar ratio of 3:1. The concentration of ICG-Sulfo-OSu at the time of reaction was specified to be 0.6 mM. After rotational agitation was performed at room temperature for 24 hours under light shielding condition, the reaction solution was filtrated with a 0.22-micrometer syringe filter, so as to obtain an aqueous solution in which the specific cyanine based dye and the PEG were covalent-bonded.

The near-infrared organic dye bonded to the PEG may be washed and refined by a known refining method, e.g., an ultrafiltration method or size exclusion column chromatography.

A compound (hereafter abbreviated to ICG-Gly) synthesized by reacting ICG-Sulfo-OSu and glycine as in Example 1 and an ICG aqueous solution (produced by Pharmaceutical and Medical Device Regulatory Science Society of Japan) were specified to be reference samples. The above-described samples were used and the retentivity in blood and the tumor accumulation were evaluated on the basis of differences in the molecular weight and the structure.

Example 5 to Example 10

The above-described ICG-Sulfo-OSu was used as the near-infrared organic dye, and 1 mg (1.25 micromoles) of ICG-Sulfo-OSu was dissolved into 100 microliters of DMSO. Meanwhile, various PEGs were weighed into 1.5-mL plastic tubes. PEG was dissolved by 50 mM carbonate buffer (pH 9.0), so that the $NH_2$ concentration was specified to be 1.25 mM. Various PEGs employed here were monoamine straight chain ME-50EA (produced by NOF CORPORATION, Mw 5,000), monoamine straight chain ME-100EA (produced by NOF CORPORATION, Mw 10,000), monoamine straight chain ME-200EA (produced by NOF CORPORATION, Mw 20,000), monoamine straight chain ME-300EA (produced by NOF CORPORATION, Mw 30,000), monoamine straight chain ME-400EA (produced by NOF CORPORATION, Mw 40,000), and diamine straight chain DE-200PA (produced by NOF CORPORATION, Mw 20,000). The covalent-bonded product of near-infrared organic dye and the PEG was produced in the same procedure as in Example 1 except that the $NH_2$ concentration was doubled. Table 6 shows the samples used in the present examples.

TABLE 6

| | Product name of PEG employed | Sample name | Molecular weight of PEG | Form |
|---|---|---|---|---|
| Example 5 | ME-50EA | M5k-ICG | 5,000 | monoamine straight chain |
| Example 6 | ME-100EA | M10k-ICG | 10,000 | monoamine straight chain |
| Example 7 | ME-200EA | M20K-ICG | 20,000 | monoamine straight chain |
| Example 8 | ME-300EA | M30k-ICG | 30,000 | monoamine straight chain |
| Example 9 | ME-400EA | M40k-ICG | 40,000 | monoamine straight chain |
| Example 10 | DE-200EA | D20k-ICG2 | 20,000 | diamine straight chain |

Photoacoustic Measurement on Mouse Body Surface

In order to examine the movement of the compound, which was prepared as described above, in the body, M5k-ICG, M10k-ICG, M20k-ICG, and M30k-ICG were administered to a nude mouse and a photoacoustic measurement of the body surface of the back of the mouse was performed. The measurement region of the photoacoustic measurement in the present example was selected in such a way that interference with main organs of the mouse did not occur. Therefore, photoacoustic signals indicate the movement of the compound present in the blood. The measurements were performed each of before administration, 60 minutes after administration, and 180 minutes after administration, and relative acoustic intensity with reference to the photoacoustic signal intensity before administration was calculated. The results of acoustic intensity measurements are summarized in Table 7, where the irradiation laser wavelength was specified to be 797 nm. Even 60 minutes after administration, the compound in which the molecular weight of PEG was more than 10 k exhibited a high photoacoustic signal equal to or higher than two times the photoacoustic signal before administration. Consequently, it was indicated that the compound bonded to PEG having a molecular weight of 10 k or more was a photoacoustic contrast medium exhibiting high retentivity in blood as compared with that in NPL 1.

TABLE 7

| | Sample name | Relative photoacoustic intensity (60 minutes after administration) | Relative photoacoustic intensity (180 minutes after administration) |
|---|---|---|---|
| Example 5 | M5k-ICG | 0.97 | 1 |
| Example 6 | M10k-ICG | 2.22 | 1 |
| Example 7 | M20k-ICG | 2.39 | 1.76 |
| Example 8 | M30k-ICG | 2.38 | 2.17 |

Movement of Compound in Body

In order to examine the retentivity in blood and the tumor accumulation of the compound prepared as described above, M5k-ICG, M10k-ICG, M20k-ICG, M30k-ICG, M40k-ICG, and D20k-ICG2 were administered to tail veins of tumor-bearing mice which had been transplanted a Colon 26 cell line. The amount of administration was specified to be 13 nmol in terms of the amount of dye.

Method for Evaluating Retentivity in Blood

A blood sample was taken from a mouse 24 hours after administration, and the blood, 1% Triron, and DMSO were mixed at 2:9:9 in a plastic tube. The amount of dye in the blood was quantified by using IVIS (registered trademark) Imaging System 200 Series (produced by Caliper Life Science Inc.) and measuring the fluorescent intensity in the state of the plastic tube. The proportion of the amount of migration of the dye to the blood relative to the amount (dye 13 nmol) of administration (% injected dose: abbreviated to % ID) per unit weight of the blood is shown in Table 8 as the retentivity of the compound in blood (% ID/g). As a result, it was ascertained that there was a tendency toward an increase in the amount of remaining blood along with an increase in the molecular weight of PEG.

Tumor Accumulation of Compound

The compound was administered to a tail vein of a tumor-bearing mouse which had been transplanted a Colon 26 cell line. The amount of administration was specified to be 13 nmol in terms of the amount of dye. A blood was taken from the mouse, and the mouse was euthanized with a carbon dioxide gas. Thereafter, a Colon 26 tumor tissue was enucleated. The resulting tumor tissue mass was subjected to tumor accumulation evaluation by the method described in Example 1. The results are shown in Table 8. Consequently, it was indicated that the tumor accumulation increased along with an increase in the molecular weight of the PEG.

TABLE 8

| | Sample name | Retentivity in blood (% ID) | Amount of tumor accumulation (% ID/g) |
|---|---|---|---|
| Example 5 | M5k-ICG | 0.1 | 1.2 |
| Example 6 | M10k-ICG | 2.8 | 5.6 |
| Example 7 | M20k-ICG | 16.8 | 12.4 |
| Example 8 | M30k-ICG | 19.8 | 12.8 |
| Example 9 | M40k-ICG | 28.8 | 16.8 |
| Example 10 | D20k-ICG2 | 10.1 | 10.5 |
| Reference example 1 | ICG-Gly | 0.2 | 0.4 |
| Reference example 2 | ICG | 0.16 | 0.1 |

Photoacoustic Imaging of Tumor Part

In order to examine the performance of imaging of a tumor, in the same manner as employed in [Evaluation of Tumor Accumulation], 26 nmol in terms of the amount of dye was administered to a tail vein of a tumor-bearing mouse which had been transplanted a Colon 26 cell line, and photoacoustic imaging was performed. In addition, a compound (hereafter abbreviated to ICG-Gly) synthesized by reacting ICG-Sulfo-OSu and glycine at a molar ratio of 1:10 was specified to be a reference sample. The photoacoustic imaging was performed 1 hour after administration, and the relative photoacoustic signal intensity with reference to the photoacoustic signal intensity of ICG-Gly was calculated. The irradiation laser wavelength was specified to be 797 nm.

TABLE 9

| | Sample name | Relative photoacoustic intensity (1 hour after administration) |
|---|---|---|
| Example 5 | M5k-ICG | 0.97 |
| Example 6 | M10k-ICG | 2.22 |
| Example 7 | M20k-ICG | 2.39 |
| Example 8 | M30k-ICG | 2.38 |
| Reference example 1 | ICG-Gly | 1 |

As is indicated from the results shown in Table 8 and Table 9, the compounds exhibited high tumor accumulation as compared with the reference sample in the tumor photoacoustic imaging, and it was indicated that the molecular weight and the structure of PEG were important parameters.

Example 11 and Example 12

Compound of Specific Cyanine Based Dye and PEG 2
Production of Marker

In the present example, the compounds represented by the formulae (7) and (8) were used as specific cyanine based compounds. The specific cyanine based dyes employed were produced by a method described in NPL 2. Dissolution of 1 mg (1.25 micromoles) of dye into 100 microliters of DMSO was performed. Meanwhile, the PEG was weighed, and the PEG was dissolved into a mixed solvent of chloroform and methanol (volume ratio 9:1), so that the $NH_2$ concentration was specified to be 0.625 mM. The chemical structural formula of the compound produced in Example 11 and the chemical structural formula of the compound produced in Example 12 were represented by the formula (I-2) and formula (I-3), respectively. The PEG derivative employed in the present examples was monoamine straight chain ME-200EA (produced by NOF CORPORATION, Mw 20,000).

The dye and the PEG were reacted at a reaction molar ratio of 2. The concentration of the dye at the time of reaction was specified to be 0.6 mM. After rotational agitation was performed at room temperature for 24 hours under light shielding condition, the solvent was removed by distillation, and redispersion into a 10-mM HEPES buffer solution was performed. In particular, the compound described in the formula (8) was not able to be dispersed alone in the water, but dispersion in the water became possible by forming a covalent bond with the PEG. The reaction solution was filtrated with a 0.22-micrometer syringe filter, so as to obtain a compound in which the specific cyanine based dye and the PEG were covalent-bonded. The compound was stored at 4 degrees Celsius under light shielding condition.

Evaluation of Movement in Body

An intravenous injection of 100 microliters (13 nmol in terms of dye) of M20k-ICGATT into a tumor-bearing mouse model was performed, where a Colon 26 cell was subcutaneously transplanted into the BALB/c Slc-nu/nu mouse. The accumulation in the Colon 26 cell mass and the blood 24 hours after the administration was evaluated by the method described in Example 12. The results thereof are summarized in Table 10. It was ascertained that the specific cyanine based dye acquired dispersibility in the water by being covalent-bonded to the PEG and exhibited tumor accumulation when this was administered into a body.

TABLE 10

| | Dye name | Amount of tumor accumulation (% ID/g) | Retentivity in blood (% ID) |
|---|---|---|---|
| Example 11 | Formula (7) | 9.95 | 18 |
| Example 12 | Formula (8) | 1.9 | 0.14 |

PEG Including Capture Molecule
Preparation of Single-Chain Antibody hu4D5-8scFv

A gene hu4D5-8scFv coding a single-chain antibody (scFv) was produced on the basis of the gene sequence (hu4D5-8) of a variable region of IgG to be bonded to HER2. Initially, cDNA was produced by connecting VL and VH genes of hu4D5-8 with cDNA coding a peptide $(GGGGS)_3$. A restriction enzyme NcoI was introduced to the 5'-terminal and the recognition site of the restriction enzyme NotI was introduced to the 3'-terminal. The base sequence was as described below.

Sequence No. 1:
5'-<u>CCATGG</u>ATATCCAGATGACCCAGTCCCCGAGCTCCCTGTCCGCCTCTG
TGGGCGATAGGGTCACCATCACCTGCCGTGCCAGTCAGGATGTGAATACTG
CTGTAGCCTGGTATCAACAGAAACCAGGAAAAGCTCCGAAACTACTGATTT
ACTCGGCATCCTTCCTCTACTCTGGAGTCCCTTCTCGCTTCTCTGGATCCA
GATCTGGGACGGATTTCACTCTGACCATCAGCAGTCTGCAGCCGGAAGACT
TCGCAACTTATTACTGTCAGCAACATTATACTACTCCTCCCACGTTCGGAC
AGGGTACCAAGGTGGAGATCAAAGGCGGTGGTGGCAGCGGTGGCGGTGGCA
GCGGCGGTGGCGGTAGCGAGGTTCAGCTGGTGGAGTCTGGCGGTGGCCTGG
TGCAGCCAGGGGGCTCACTCCGTTTGTCCTGTGCAGCTTCTGGCTTCAACA
TTAAAGACACCTATATACACTGGGTGCGTCAGGCCCCGGGTAAGGGCCTGG
AATGGGTTGCAAGGATTTATCCTACGAATGGTTATACTAGATATGCCGATA
GCGTCAAGGGCCGTTTCACTATAAGCGCAGACACATCCAAAAACACAGCCT
ACCTGCAGATGAACAGCCTGCGTGCTGAGGACACTGCCGTCTATTATTGTT
CTAGATGGGAGGGGACGGCTTCTATGCTATGGACTACTGGGGTCAAGGAA
CCCTGGTCACCGTCTCCTCGG<u>CGGCCGC</u>-3'

(The Recognition Site of the Restriction Enzyme is Underlined)

The above-described gene segment hu4D5-8scFv was inserted downstream of a T7/lac promoter of a plasmid pET-22b(+) (produced by Novagen). Specifically, the above-described cDNA was ligated to pET-22b(+) subjected to a digestion treatment with the restriction enzymes NcoI and NotI.

This expression plasmid was transformed to *Escherichia coli* BL21(DE3), so as to obtain an expression strain. The resulting strain was precultured for a night in 4 ml of LB-Amp culture medium, the whole quantity was added to 250 ml of 2×YT culture medium, and shake culture was performed at 28 degrees Celsius and 120 rpm for 8 hours. Thereafter, Isopropyl-beta-D(−)-thiogalactopyranoside (IPTG) was added in such a way that the final concentration became 1 mM and culture was performed for a night at 28 degrees Celsius. The cultured *Escherichia coli* was subjected to centrifugal separation with 8,000×g for 30 minutes at 4 degrees Celsius, and a supernatant culture fluid thereof was recovered. Ammonium sulfate 60% of the resulting culture fluid in weight was added, so as to precipitate proteins through salting out. The solution subjected to the salting out operation was stood for a night at 4 degrees Celsius and was subjected to centrifugal separation at 8,000×g for 30 minutes at 4 degrees Celsius, so as to recover precipitates. The resulting precipitates were dissolved into 20 mM Tris-HCL/500 mM NaCl buffer and was dialyzed into 1 L of the same type of buffer. The protein solution after dialysis was added to a column filled with His-Bind (registered trademark) Resin (produced by Novagen) and was refined by metal chelate affinity chromatography through Ni ions. It was ascertained that the refined hu4D5-8scFv exhibited a single band on the basis of the reduced SDS-PAGE and the molecular weight was about 28 kDa. The amino acid sequence of the prepared antibody is as described below. Hereafter hu4D5-8scFv is abbreviated to scFv.

Sequence No. 2

DIQMTQSPSSLSASVGDRVTITCRASQDVNTAVAWYQQKPGKAPKLLIYSA

SFLYSGVPSRFSGSRSGTDFTLTISSLQPEDFATYYCQQHYTTPPTFGQGT

KVEIKGGGGSGGGGSGGGGSEVQLVESGGGLVQPGGSLRLSCAASGFNIKD

TYIHWVRQAPGKGLEWVARIYPTNGYTRYADSVKGRFTISADTSKNTAYLQ

MNSLRAEDTAVYYCSRWGGDGFYAMDYWGQGTLVTVSSAAALEHHHHHHGG

C

Modification of PEG with scFv

The buffer of scFv prepared as described above was substituted with a phosphate buffer (2.68 mM KCl/137 mM NaCl/1.47 mM KH2PO4/1 mM Na2HPO4/5 mM EDTA, pH 7.4) containing 5 mM of EDTA. Thereafter, a reduction treatment was performed with tri(2-carboxyethyl)phosphine hydrochloride (TCEP) in the amount of 10 times on a mole basis at 25 degrees Celsius for about 2 hours.

Meanwhile, monomaleimide straight chain ME-400MA (produced by NOF CORPORATION, MW 40,000) was weighed into a 1.5-mL plastic tube. Dilution was performed with a phosphate buffer not containing EDTA to become 17.9 micromolars, mixing was performed with scFv subjected to the above-described reduction treatment and, then, a reaction was induced at 25 degrees Celsius for 15 hours or more. The reaction molar ratio (scFv/PEG) was specified to be 1 on a charge basis. Here, the term "charge" refers to addition to the reaction system, and the term "reaction molar ratio on a charge basis" refers to the molar concentration ratio of scFv to PEG added to the reaction system. Subsequently, a solution (12.5 mM), ICG-Sulfo-OSu in DMSO, was mixed with the above-described mixed solution of scFv and PEG, and a reaction was induced at 25 degrees Celsius for 2 hours. The reaction molar ratio (ICG-Sulfo-OSu/scFv) was specified to be 3 on a charge basis. The resulting solution was filtrated with a filter (pore size 1.2 micrometers) and, thereafter, scFv not bonded to the PEG was removed by ultrafiltration using Amicon Ultra-4 (produced by Nihon Millipore K.K.) having a pore size of 30 kDa, so as to obtain a PEG modified with ICG and scFv. The thus obtained compound is abbreviated to scFv-PEG40.

Modification of PEG with Affibody (Registered Trademark)

A dithiothreitol (DTT) solution was added to a solution (produced by Affibody) of Affibody (registered trademark) to be bonded to HER2 in such a way that the final concentration became 20 mM, and a reduction treatment was performed at 25 degrees Celsius for 2 hours under light shielding condition. DTT was removed from the reaction solution by using a PD-10 column (produced by GE Healthcare). Monomaleimide straight chain ME-200MA (produced by NOF CORPORATION, MW 20,000) and monomaleimide straight chain ME-400MA (produced by NOF CORPORATION, MW 40,000) were weighed into 1.5-mL plastic tubes independently. The weighed PEG was diluted with a phosphate buffer not containing EDTA to become 143 micromolars and was mixed with Affibody (registered trademark) subjected to the above-described reduction treatment. Then, a reaction was induced at 25 degrees Celsius for 15 hours or more. The reaction molar ratio (Affibody (registered trademark)/PEG) was specified to be 1 on a charge basis. A solution (12.5 mM), ICG-Sulfo-OSu in DMSO, was mixed with the above-described mixed solution of Affibody (registered trademark) and PEG, and a reaction was induced at 25 degrees Celsius for 2 hours. The reaction molar ratio (ICG-Sulfo-OSu/Affibody (registered trademark)) was specified to be 1 on a charge basis. The resulting solution was filtrated with a filter (pore size 1.2 micrometers) and, thereafter, Affibody (registered trademark) not bonded to the PEG was removed by ultrafiltration using Amicon Ultra-4 (produced by Nihon Millipore K.K.) having a pore size of 10 kDa, so as to obtain PEGs modified with ICG and Affibody (registered trademark). Among the thus obtained compounds, the compound by using ME-200MA is abbreviated to Af-PEG20 and the compound by using ME-400MA is abbreviated to Af-PEG40.

Modification of PEG with Peptide

A peptide was synthesized (Sequence No. 3) in which 6 amino acids were imparted to carboxyl terminals of a peptide sequence having an ensured property to bond to HER2. A cysteine residue present at a carboxyl terminal of this peptide sequence can react with a maleimide group so as to form a covalent bond.

Sequence No. 3

MARSGLGGKGSC

Monomaleimide straight chain ME-200MA (produced by NOF CORPORATION, MW 20,000) and monomaleimide straight chain ME-400MA (produced by NOF CORPORATION, MW 40,000) were weighed into 1.5-mL plastic tubes independently. The weighed PEG was diluted with a phosphate buffer not containing EDTA to become 1.57 mM and was mixed with the above-described peptide solution. Then, a reaction was induced at 25 degrees Celsius for 15 hours or more. The reaction molar ratio (peptide/PEG) was specified to be 1 on a charge basis. A solution (12.5 mM), ICG-Sulfo-OSu in DMSO, was mixed with the above-described mixed solution of the peptide and PEG, and a reaction was induced at 25 degrees Celsius for 2 hours. The reaction molar ratio (ICG-Sulfo-OSu/peptide) was specified to be 1 on a charge basis. The resulting solution was filtrated with a filter (pore size 1.2 micrometers) and, thereafter, the peptide not bonded to the PEG was removed by ultrafiltration using Amicon Ultra-4 (produced by Nihon Millipore K.K.) having a pore size of 10 kDa, so as to obtain PEGs modified with ICG and the peptide. Among the thus obtained compounds, the compound by using ME-200MA is abbreviated to pe-PEG20 and the compound by using ME-400MA is abbreviated to pe-PEG40.

Evaluation of Bonding Property of PEG Including Capture Molecule to HER2

The bonding property of the PEG including the capture molecule to HER2 serving as a target molecule was evaluated by a surface plasmon resonance method (SPR). In SPR, the measurement was performed using Proteon (registered trademark) XPR36 (produced by Bio-Rad Laboratories). Recombinant Human ErbB2/Fc Chimera (produced by R&D Systems) was dissolved into an acetate buffer (pH 5.0), and was immobilized by amine coupling to a carboxyl group on the GLM sensor chip surface. The amount of immobilization was about 3,000 RU (Resonance Unit). Subsequently, the PEG including the capture molecule was diluted to various concentrations with a phosphate buffer (pH 7.4) containing 0.005% of Tween20 and was injected into a flow cell at a flow rate of 50 microliters/min. As for the measurement times, an injection time (bonding) was 120 seconds and an elapsed time after stopping of injection (dissociation) was 120 seconds. In a bonding kinetic analysis experiment, sensor grams were analyzed using 1:1 Langmuir fitting model. The calculated binding dissociation constants ($K_D$) are collectively shown in Table 11. The bonding property to HER2 was ensured with respect to every sample. In particular, strong bonding property was ensured with respect to scFv-PEG40, Af-PEG20, and Af-PEG40.

TABLE 11

| Sample name | Product name of PEG employed | Type of capture molecule | Molecular weight of PEG | $K_D$ [nM] |
|---|---|---|---|---|
| scFv-PEG40 | ME-200MA | scFv | 40000 | 4.2 |
| Af-PEG20 | ME-200MA | Affibody (registered trademark) | 20000 | 9.7 |
| Af-PEG40 | ME-400MA | Affibody (registered trademark) | 40000 | 2.3 |
| pe-PEG20 | ME-200MA | peptide | 20000 | 2600 |
| pe-PEG40 | ME-400MA | peptide | 40000 | 3100 |

Evaluation of Tumor Accumulation of PEG Including Capture Molecule

In the evaluation of tumor accumulation, female outbred line BALB/c Slc-nu/nu mouse (6 week-old at the time of purchase) (Japan SLC Inc.) was used. The mouse was adapted to an environment in which a diet and drinking water were able to be consumed freely for a week before the mouse was transplanted a tumor, while standard diet and bed were employed. About 1 week before an imaging experiment, $1\times10^6$ of Colon 26 mouse colon cancer cells (RIKEN) were subcutaneously injected into each of the right shoulder and the right thigh of the mouse and $1\times10^6$ of Colon 26 mouse colon cancer cells containing artificially introduced HER2 genes were subcutaneously injected into each of the left shoulder and the left thigh of the mouse. All tumors became established until the experiment and the weights of the mice were 17 to 22 g. An intravenous injection of 200 microliters (13 nmol in terms of ICG) of PEG including the capture molecule or D20k-ICG2 into tumor-bearing mice was performed. The mice were euthanized with a carbon dioxide gas 24 hours after the administration. Subsequently, each cancer tissue was enucleated. The cancer tissue was transferred to a plastic tube, 1% Triton-X100 aqueous solution 1.25 times the cancer tissue in weight was added, and a homogenate was produced using a plastic pestle. Thereafter, DMSO 20.25 times the cancer tissue in weight was added, so as to prepare a solution of dye extracted from the tumor tissue. Meanwhile, cancer tissue was enucleated from the tumor-bearing mouse not administered the PEG including the capture molecule. The cancer tissue was transferred to a plastic tube, 1% Triton-X100 aqueous solution 1.25 times the cancer tissue in weight was added, and a homogenate was produced using a plastic pestle, so as to prepare a Triton X100 solution containing the tumor tissue. Then, the solution of a known concentration of PEG including the capture molecule was diluted to various concentrations with the above-described Triton-X100 solution containing the cancer tissue. A standard solution for calibration was prepared by adding DMSO 20.25 times the resulting diluted solution in amount. The amount of dye in the cancer tissue was quantified by using IVIS (registered trademark) Imaging System 200 Series (XENOGEN) and measuring the fluorescent intensity of the solution of dye extracted from the tumor tissue and the standard solution for calibration in the state of the plastic tube.

In the above-described evaluation of the tumor accumulation, just before the mouse was euthanized with a carbon dioxide gas 24 hours after the administration, blood was taken from the tail vein. The resulting blood was transferred to a plastic tube, 1% Triton-X100 aqueous solution 4.5 times the blood in volume was added. Thereafter, DMSO 4.5 times the blood in volume was added, so as to prepare a blood-containing solution. The fluorescent intensity of the blood-containing solution was measured by using IVIS (registered trademark) Imaging System 200 Series (XENOGEN) in the state of the plastic tube. Meanwhile, the particle solution having a known concentration was diluted to various concentrations with the 1% Triton-X100 aqueous solution. The diluted particle solution and an equal amount of blood taken from a mouse not administered were mixed. Subsequently, 1% Triton-X100 aqueous solution was added in such a way that the volume including the volume of the above-described diluted particle solution became 4.5 times the volume of blood. Then, a blood particle solution for calibration curve was produced by adding DMSO 4.5 times the blood in volume. The fluorescent intensity was measured and a calibration curve was formed as with the taken blood sample. Next, the concentration in the blood was calculated by using the fluorescent intensity of the blood-containing solution and the calibration curve formed. Each of the calculated concentrations in the blood was divided by the total amount of administration, so as to calculate the proportion of the abundance in the blood per amount of administration (% ID).

Figure 3:
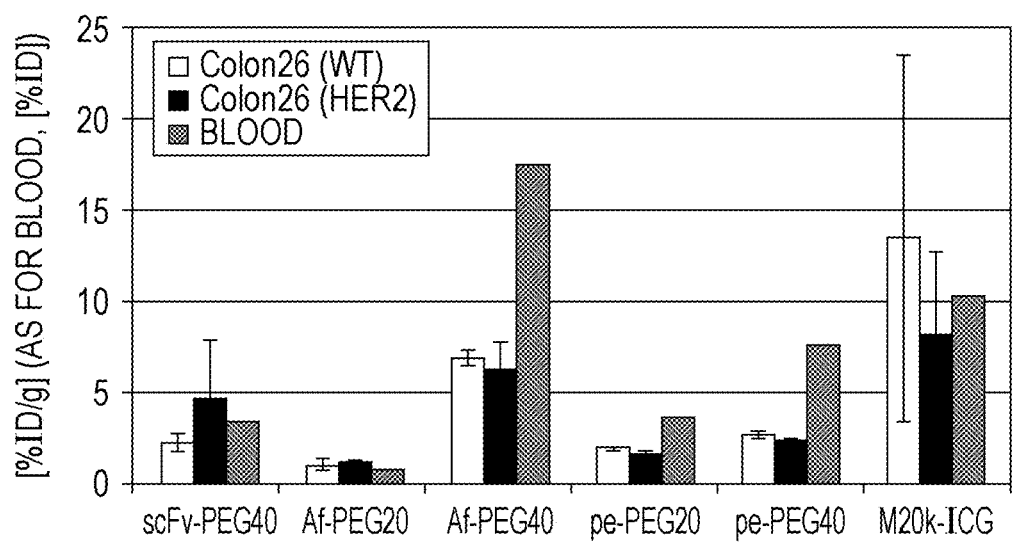
FIG. 3 is a graph showing the results obtained in an evaluation experiment of the tumor accumulation performed in an example according to an aspect of the present invention.

The results of the tumor accumulation and the results of the abundance in the blood are summarized in FIG. 3. The amount of accumulation into the Colon 26 mouse colon cancer cell was indicated by white, the amount of accumulation into the Colon 26 mouse colon cancer cell containing artificially introduced HER2 genes was indicated by black, and the proportion of the abundance in the blood per amount of administration was indicated by gray.

All the PEGs including the capture molecule exhibited tendencies toward a decrease in the tumor accumulation as compared with D20k-ICG2. However, as for Af-PEG40, it was able to be ascertained that the tumor accumulation and the abundance in the blood stood comparison therewith. In addition, ratios of the amount of accumulation into the Colon 26 mouse colon cancer cells containing artificially introduced HER2 genes relative to the amount of accumulation into the Colon 26 mouse colon cancer cells were calculated and are summarized in Table 12. The amounts of accumulation of all the PEGs including the capture molecule into the Colon 26 mouse colon cancer cells containing artificially introduced HER2 genes were large as compared with those of D20k-ICG2. Therefore, an effect of the capture molecule on the property to bond to HER2 was ascertained.

TABLE 12

| Sample name | Colon26 (HER2)/Colon26 (WT) Ratio of amount of tumor accumulation |
|---|---|
| scFv-PEG40 | 2.0 |
| Af-PEG20 | 1.1 |
| Af-PEG40 | 0.91 |
| pe-PEG20 | 0.76 |
| pe-PEG40 | 0.88 |
| M20k-ICG | 0.60 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-161642, filed Jul. 20, 2012, which is hereby incorporated by reference herein in its entirety.

The invention claimed is:

1. A compound represented by formula (IV):

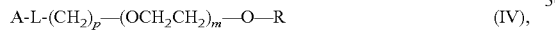

wherein, in the formula (IV), A represents any one of formula (i) to formula (vi), and * in the formulae (i) to (vi) represents a bond with $L^1$ in the formula (IV), wherein, in the formula (IV), $L^1$ represents a linker part which is any one of —NH—, —O—, —S—, and —CO— or which contains at least one of —NH—, —O—, —S—, and —CO—, p represents an integer of 1 to 5, m represents an integer of 10 to 2,500, and R represents any one of a hydrogen atom and a substituted or unsubstituted alkyl group having 1 to 5 carbon atoms,

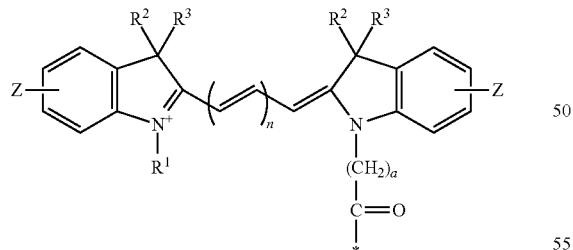

(i)

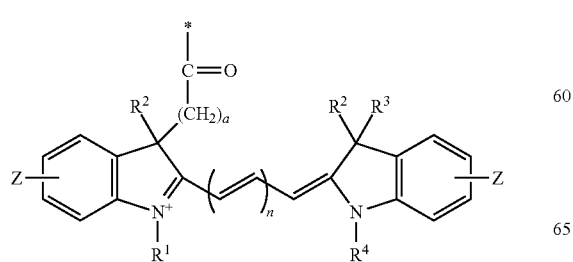

(ii)

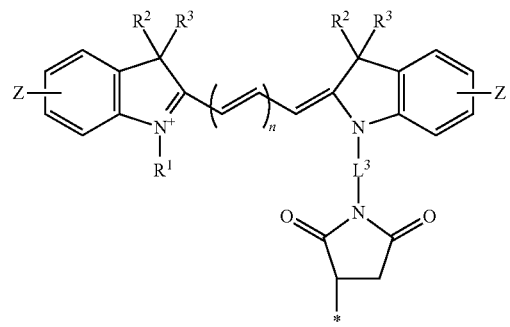

(iii)

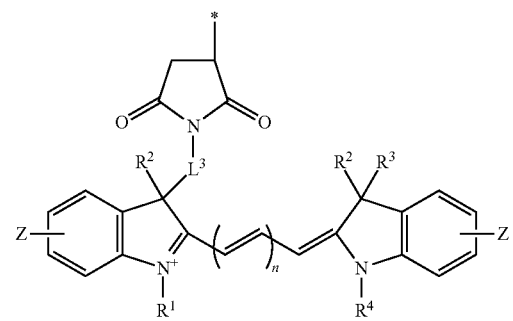

(iv)

-continued

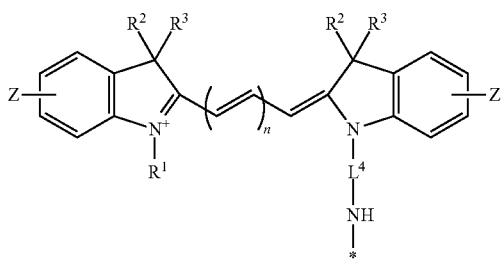
(v)

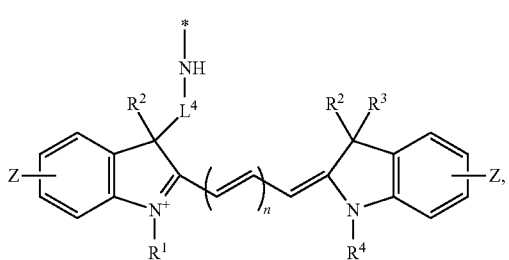
(vi)

wherein, in the formulae (i) to (vi), Z forms a cyclic aromatic ring composed of a benz[e]indole ring, benz[f]indole ring, or benz[g]indole ring together with a hydrogen atom, a sulfonate group, or an indole ring bonded to Z, and furthermore, a hydrogen atom of the cyclic aromatic ring may be substituted with an alkyl group having 1 to 10 carbon atoms, an alkoxy group having 1 to 10 carbon atoms, or a sulfonate group, wherein, in the formulae (i) to (vi), $R^1$ represents any one of an alkyl group having 1 to 10 carbon atoms and $-(CH_2)_b-SO_3^-$, where b represents an integer of 1 to 10, and when $R^1$ is an alkyl group, a halogen ion or an organic acid ion may be contained as a counter ion, and $R^2$ and $R^3$ represent independently any one of a hydrogen atom, an alkyl group having 1 to 10 carbon atoms, an alkoxy group having 1 to 10 carbon atoms, $-(CH_2)_b-SO_3^-$, where b represents an integer of 1 to 10, and $-(CH_2)_b-SO_3X$, where b represents an integer of 1 to 10 and X represents any one of sodium, potassium, ammonium, triethylammonium, lysine, and arginine, wherein, in the formulae (i) and (ii), a represents an integer of 1 to 10, wherein, in the formulae (i) to (vi), n represents 2 or 3, wherein, in the formulae (ii), (iv), and (vi), $R^4$ represents any one of an alkyl group having 1 to 10 carbon atoms and $-(CH_2)_b-SO_3X$, where b represents an integer of 1 to 10 and X represents any one of sodium, potassium, ammonium, triethylammonium, lysine, and arginine, wherein, in the formulae (iii) and (iv), $L^3$ represents a substituted or unsubstituted alkyl group which has 1 to 10 carbon atoms and which may include a carbonyl group, an amide group, an ester group, or a piperazyl group as a substituent, and wherein, in the formulae (v) and (vi), $L^4$ represents a substituted or unsubstituted alkyl group which has 1 to 10 carbon atoms and which may include a carbonyl group, an amide group, or an ester group as a substituent.

2. The compound according to claim 1, wherein m in the formula (IV) is an integer of 100 to 500.

3. The compound according to claim 1, wherein A in the formula (IV) is represented by the formula (i).

4. The compound according to claim 1, wherein the formula (i) is represented by any one of formulae (i-1) to (i-6):

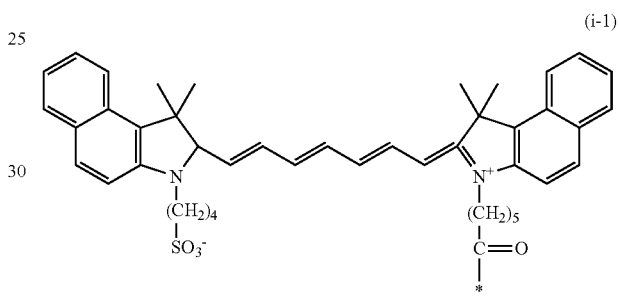
(i-1)

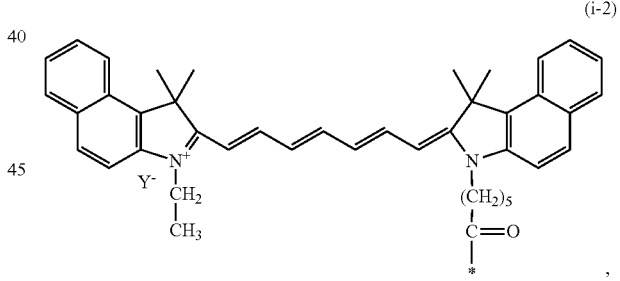
(i-2)

wherein, in the formula (i-2), Y represents a halogen ion or an organic acid ion,

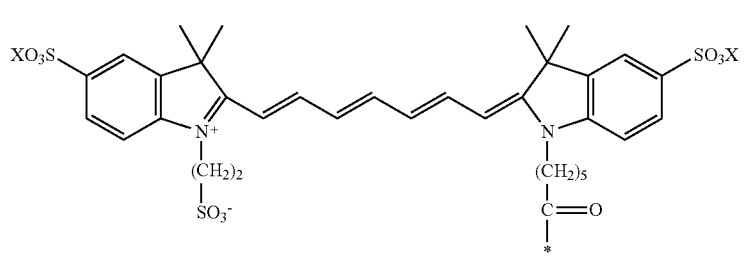
(i-3)

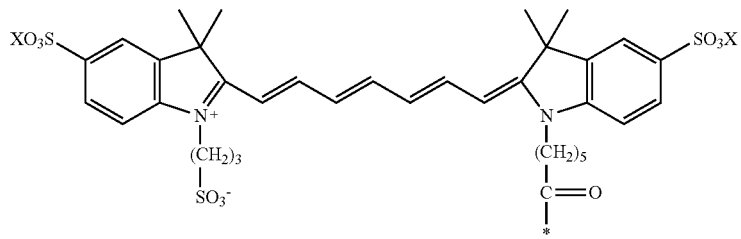
(i-4)
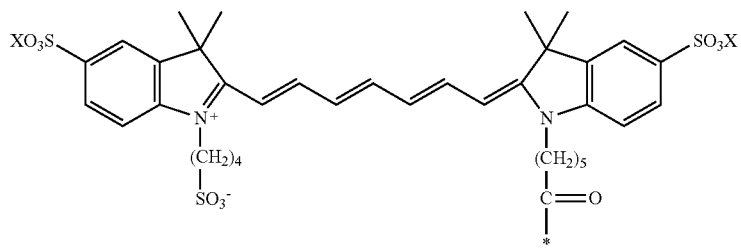
(i-5)
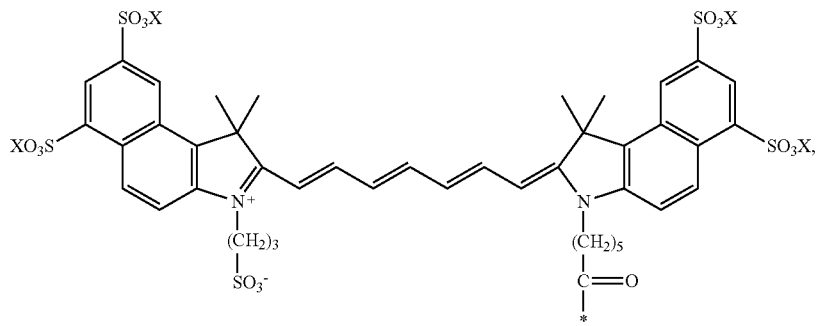
(i-6)
wherein, in the formulae (i-3) to (i-6), X represents any one of sodium, potassium, ammonium, triethylammonium, lysine, and arginine.
5. The compound according to claim 1, wherein the formula (ii) is represented by formula (ii-1) or formula (ii-2):
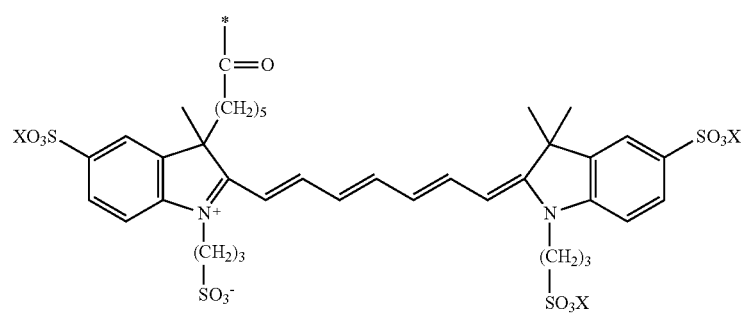
(ii-1)
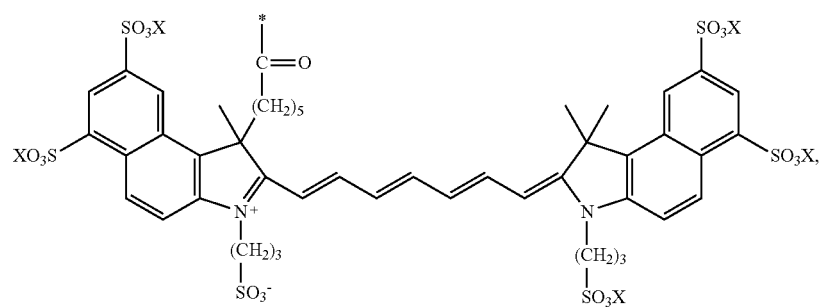
(ii-2)

wherein, in the formulae (ii-1) to (ii-2), X represents any one of sodium, potassium, ammonium, triethylammonium, lysine, and arginine.

6. The compound according to claim 1, wherein the formula (iii) is represented by formula (iii-1) or formula (iii-2):

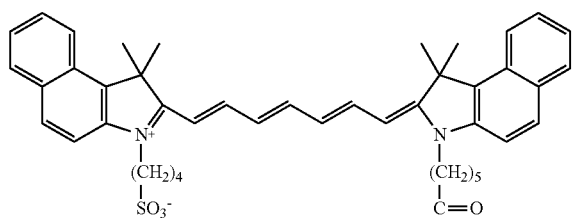

(iii-1)

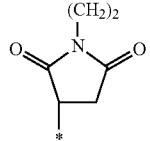

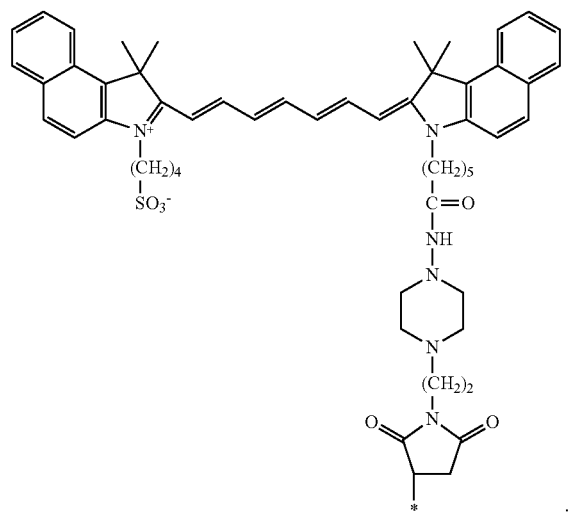

(iii-2)

7. The compound according to claim 1, wherein the formula (iv) is represented by formula (iv-1) or formula (iv-2):

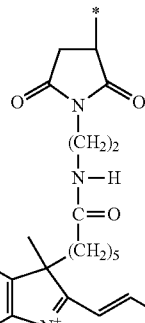

(iv-1)

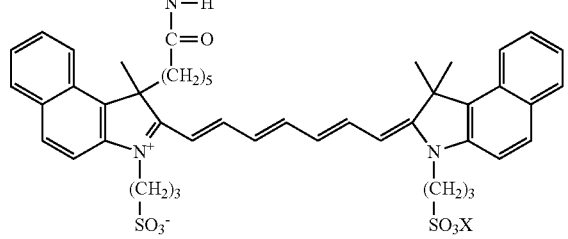

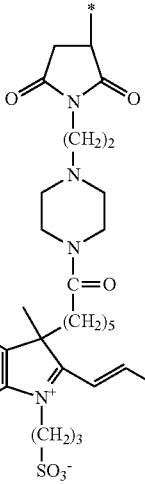

(iv-2)

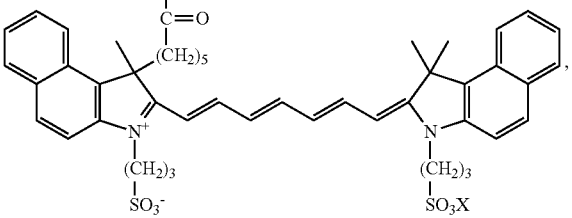

wherein, in the formulae (iv-1) to (iv-2), X represents any one of sodium, potassium, ammonium, triethylammonium, lysine, and arginine.

8. The compound according to claim 1, further comprising a capture molecule.

9. The compound according to claim 8, wherein the linker part is the capture molecule.

10. The compound according to claim 9, wherein the capture molecule is any one of a polypeptide or a single-chain antibody.

11. The compound according to claim 1, wherein $L^1$ is represented by formula (xi):

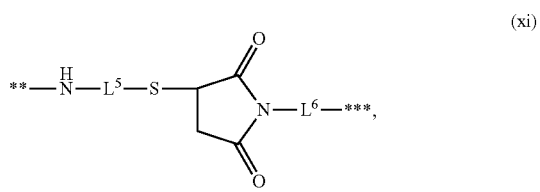

(xi)

wherein, in the formula (xi), $L^5$ represents a polypeptide or a single-chain antibody, —NH— represents a bond through an amino group of an amino acid in the polypeptide or the single-chain antibody, —S— represents a bond through a thiol group of an amino acid in the polypeptide or the single-chain antibody, $L^6$ represents an alkyl chain which has 1 to 10 carbon atoms and which may include any one of a carbonyl group, an amide group, an ester group, and a piperazyl group as a substituent, ** represents a bond with *, and *** represents a bond with the alkyl chain side or the ethylene glycol chain side of the formula (IV).

12. The compound according to claim 1, wherein $L^6$ in the formula (xi) is represented by formula (xii):

$$-(CH_2)_2-C(=O)-NH- \qquad (xii),$$

wherein, in the formula (xii), carbon in the ethylene group is bonded to nitrogen in the maleimide group in the formula (xi), and nitrogen in —NH— is bonded at *** in the formula (xi).

13. A photoimaging contrast medium comprising the compound according to claim 1 and a dispersion medium.

14. The photoimaging contrast medium according to claim 13, further comprising an addition agent.

* * * * *